(12) United States Patent
Jurak et al.

(10) Patent No.: US 11,291,739 B2
(45) Date of Patent: Apr. 5, 2022

(54) SYSTEM AND METHODS FOR STERILIZING ENCLOSED SPACES USING OZONE

(71) Applicant: Gene Therapy Systems, Inc., San Diego, CA (US)

(72) Inventors: Steven J. Jurak, San Diego, CA (US); Anthony M. Sorge, Sr., Rancho Santa Fe, CA (US)

(73) Assignee: Gene Therapy Systems, Inc., San Diego, CA (US)

( * ) Notice: Subject to any disclaimer, the term of this patent is extended or adjusted under 35 U.S.C. 154(b) by 0 days.

(21) Appl. No.: 17/031,014

(22) Filed: Sep. 24, 2020

(65) Prior Publication Data

US 2021/0015953 A1    Jan. 21, 2021

Related U.S. Application Data

(63) Continuation of application No. 15/265,729, filed on Sep. 14, 2016, now Pat. No. 10,786,588.

(Continued)

(51) Int. Cl.
*A61L 2/20* (2006.01)
*A61L 9/22* (2006.01)
(Continued)

(52) U.S. Cl.
CPC ............... *A61L 2/202* (2013.01); *A61L 2/10* (2013.01); *A61L 9/20* (2013.01); *A61L 9/22* (2013.01);
(Continued)

(58) Field of Classification Search
CPC ..... A61L 2/202; A61L 2/10; A61L 9/22; A61L 9/20; A61L 2202/14; A61L 2202/25;
(Continued)

(56) References Cited

U.S. PATENT DOCUMENTS

| 2,453,435 A | 11/1948 | Havstad |
| 5,024,766 A | 6/1991 | Mahmud |

(Continued)

FOREIGN PATENT DOCUMENTS

| CN | 103977441 | 8/2014 |

OTHER PUBLICATIONS

Chemical Sampling Information | Ozone; NIOSH Pocket Guide to Chemical Hazards; United States Department of Labor Occupational Safety & Health Administration; OSHA IMIS Code No. 1980; Jan. 6, 2012; www.osha.gov/dts/chemicalsampling/data/CH_259300.html.

(Continued)

*Primary Examiner* — Regina M Yoo
(74) *Attorney, Agent, or Firm* — Knobbe, Martens, Olson & Bear, LLP

(57) ABSTRACT

Systems and methods for sterilizing an enclosed space using ozone are disclosed herein. Various embodiments of the devices and methods also provide for accelerated degradation of the ozone upon sterilization. The methods can include identifying enclosed spaces, sterilizing enclosed spaces through ozone generation, generating reports and transmitting the reports. The sterilization unit disclosed herein can sterilize a plurality of enclosed spaces, such as a fleet of medical response vehicles.

18 Claims, 11 Drawing Sheets

Related U.S. Application Data

(60) Provisional application No. 62/218,926, filed on Sep. 15, 2015.

(51) Int. Cl.
*A61L 9/20* (2006.01)
*A61L 2/10* (2006.01)

(52) U.S. Cl.
CPC ........ *A61L 2202/11* (2013.01); *A61L 2202/13* (2013.01); *A61L 2202/14* (2013.01); *A61L 2202/16* (2013.01); *A61L 2202/25* (2013.01); *A61L 2209/111* (2013.01); *A61L 2209/14* (2013.01); *A61L 2209/212* (2013.01)

(58) Field of Classification Search
CPC ............. A61L 2202/13; A61L 2202/16; A61L 2209/14; A61L 2202/11; A61L 2209/212; A61L 2209/111
See application file for complete search history.

(56) References Cited

U.S. PATENT DOCUMENTS

| | | | |
|---|---|---|---|
| 5,368,816 A | 11/1994 | Detzer | |
| 6,481,219 B2 | 11/2002 | Palermo | |
| 6,485,978 B1 * | 11/2002 | Kirckof | A61L 2/28 422/403 |
| 7,407,624 B2 | 8/2008 | Cumberland | |
| 7,693,687 B2 | 4/2010 | Lev-Ami et al. | |
| 7,982,625 B2 | 7/2011 | Brochu et al. | |
| 8,236,236 B2 | 8/2012 | Garner | |
| 8,354,057 B2 | 1/2013 | Heselton | |
| 8,388,900 B2 * | 3/2013 | Benedek | A61L 9/015 422/186.07 |
| 8,865,065 B2 | 10/2014 | Kain et al. | |
| 9,623,140 B2 | 4/2017 | Jurak et al. | |
| 9,987,388 B2 | 6/2018 | Jurak et al. | |
| 10,786,588 B2 | 9/2020 | Jurak et al. | |
| 10,980,910 B2 | 4/2021 | Jurak et al. | |
| 2002/0058001 A1 | 5/2002 | Wu | |
| 2003/0127506 A1 | 7/2003 | Braun | |
| 2003/0152480 A1 | 8/2003 | Sham | |
| 2004/0047776 A1 | 3/2004 | Thomsen | |
| 2004/0202570 A1 | 10/2004 | Nadkarni | |
| 2004/0262241 A1 | 12/2004 | Socha | |
| 2005/0123436 A1 | 6/2005 | Cumberland | |
| 2008/0031770 A1 | 2/2008 | Heselton | |
| 2008/0159910 A1 | 7/2008 | Dick et al. | |
| 2008/0213125 A1 | 9/2008 | Boast | |
| 2008/0213128 A1 | 9/2008 | Rudy et al. | |
| 2008/0310992 A1 | 12/2008 | Heselton | |
| 2010/0152911 A1 | 6/2010 | Brochu et al. | |
| 2010/0178196 A1 | 7/2010 | Garner | |
| 2011/0008205 A1 | 1/2011 | Mangiardi | |
| 2011/0268606 A1 | 11/2011 | Glazer et al. | |
| 2012/0020830 A1 | 1/2012 | Boast et al. | |
| 2012/0063949 A1 | 3/2012 | Jennings | |
| 2012/0316402 A1 * | 12/2012 | Salapatek | A61G 10/02 600/300 |
| 2013/0183749 A1 | 7/2013 | Aamodt et al. | |
| 2013/0224072 A1 | 8/2013 | Glazer et al. | |
| 2014/0193294 A1 * | 7/2014 | Kain | A61L 2/202 422/3 |
| 2014/0193296 A1 * | 7/2014 | Jurak | A61L 2/202 422/4 |
| 2014/0234165 A1 * | 8/2014 | Glazer | A61L 11/00 422/38 |
| 2017/0072082 A1 | 3/2017 | Jurak et al. | |
| 2017/0281823 A1 | 10/2017 | Jurak et al. | |
| 2019/0030204 A1 | 1/2019 | Jurak et al. | |

OTHER PUBLICATIONS

English Translation of CN-103977441-A (Year: 2014).

* cited by examiner

Company Report

1  Customer #058582016-1
2  Location San Diego
3  Sterilization Unit 100016

Report Data Period
4  August 1-31, 2016
5  Beacon ID #12
6  01234560-1200-3000-1648-768445

| | Date | Time | O3 t | O3 | Scrub T | O3L | Unit Hours |
|---|---|---|---|---|---|---|---|
| 7 | 9/2/16 | 10:21 | 90 | Pass | 30 | .01 | 166 |
| 8 | 9/8/16 | 8:51 | 60 | Pass | 30 | .02 | 190 |
| 9 | 9/12/16 | 11:01 | 42 | FAIL | 30 | .01 | 201 |
| 10 | 9/21/16 | 9:34 | 90 | Pass | 15 | .01 | 223 |
| 11 | 9/29/16 | 10:01 | 90 | Pass | 30 | .01 | 241 |

Report Data Period
12  August 1-31, 2016
13  Beacon ID #13
14  01234560-1200-4000-1628-768485

| | Date | Time | O3 t | O3 | Scrub T | O3L | Unit Hours |
|---|---|---|---|---|---|---|---|
| 15 | 9/3/16 | 12:01 | 90 | Pass | 30 | .01 | 169 |
| 16 | 9/8/16 | 13:41 | 90 | Pass | 30 | .02 | 188 |
| 17 | 9/14/16 | 14:45 | 90 | Pass | 30 | .01 | 210 |
| 18 | 9/22/16 | 12:18 | 90 | Pass | 30 | .01 | 233 |
| 19 | 9/30/16 | 11:51 | 90 | Pass | 30 | .01 | 252 |

Report Data Period
August 1-31, 2016
Beacon ID #114
01232560-1600-3000-1648-868442

| Date | Time | O3 t | O3 | Scrub T | O3L | Unit Hours |
|---|---|---|---|---|---|---|
| 9/1/16 | 11:21 | 90 | Pass | 30 | .01 | 172 |
| 9/7/16 | 8:31 | 90 | Pass | 30 | .02 | 196 |
| 9/14/16 | 13:01 | 90 | Pass | 30 | .01 | 209 |
| 9/24/16 | 9:14 | 90 | Pass | 30 | .01 | 233 |
| 9/31/16 | 10:41 | 90 | Pass | 30 | .01 | 261 |

FIG. 8

SYSTEM AND METHODS FOR STERILIZING ENCLOSED SPACES USING OZONE

CROSS-REFERENCE TO RELATED APPLICATIONS

The present application is a continuation of U.S. patent application Ser. No. 15/265,729, filed Sep. 14, 2016 and scheduled to issue as U.S. Pat. No. 10,786,588 on Sep. 29, 2020, which claims priority under 35 U.S.C. § 119(e) to U.S. Provisional Patent Application No. 62/218,926, filed on Sep. 15, 2015, which is hereby incorporated by reference in its entirety, including any drawings. The present application is related to U.S. Provisional Patent Application No. 61/751,125, filed on Jan. 10, 2013, and U.S. patent application Ser. No. 14/151,608, filed on Jan. 9, 2014, each of which is hereby incorporated by reference in its entirety.

BACKGROUND

Field

The present disclosure relates to sterilization systems and methods, and particularly, to systems and methods for identifying enclosed spaces, sterilizing the identified enclosed spaces through ozone generation, generating reports regarding the sterilization procedures, and transmitting the reports. Sterilization units and systems disclosed herein can sterilize a plurality of enclosed spaces, such as enclosed spaces of varying sizes in a fleet of medical response vehicles situated in different locations.

Description of the Related Art

The removal of harmful or irritating contaminants, such as, for example, bacteria, viruses, bacteriophages, molds, spores, and cigarette smoke particulates, is a common goal in many areas where such contaminants proliferate. Within many environments, such as, for example, ambulances, mobile hospitals, life flight helicopters, urgent and non-urgent vehicles for medical transport, hospital rooms, airplanes, gyms, hotel rooms, rental cars, and laboratory and medical equipment, the presence of such contaminants can lead to harmful and/or disruptive results. For example, in ambulances, hospital rooms and other healthcare facilities, sick patients introduce illness-causing bacteria and viruses into the air regularly. The presence of such contaminants is particularly dangerous in healthcare facilities where many patients have compromised immune systems that render them more susceptible to the contaminants' potentially adverse health effects. Additionally, in laboratory settings, spores, mold, bacteria, viruses, bacteriophages, and other foreign biological materials can contaminate test cultures, leading to inaccurate test results, costly delays, and potentially, loss of non-reproducible parent cultures.

Various methods currently exist for decontaminating enclosed spaces. In one method, a spray disinfectant is sprayed onto the surfaces of an enclosed space and wiped away. This method is time-intensive, requires frequent repetition, and limits disinfection to accessible surfaces. Biological materials present in the air and on difficult to reach surfaces often remain untouched. Additionally, commonly-used disinfecting agents are either limited in effectiveness or cytotoxic. Such a method may expose individuals doing the cleaning to chemicals harmful to their health. In another method, an ultraviolet radiator is used to disinfect a small enclosed space, such as a laboratory incubator or laboratory laminar flow hood. In such a method, disinfection is only possible in places directly exposed to the ultraviolet light. Steam-in-place sterilization is available in some laboratory settings, such as, for example, in laboratory hoods, incubators, and reaction vessels; however, the method is impractical in many environments. Steam-in-place sterilization can only be used within equipment capable of withstanding moisture and extremely high temperatures (approximately 100-180 degrees Celsius). Additionally, steam-in-place sterilization requires the installation of expensive steam-producing equipment. Other sterilization methods, such as sterilization within an ozone chamber or autoclave chamber are designed to sterilize objects placed within a sterilization chamber, making the method unusable for the decontamination of fixtures, rooms, large equipment, and other immobile and/or bulky items.

SUMMARY

A need exists for an effective, safe, convenient, and relatively low-cost sterilization method capable of thoroughly sterilizing an enclosed space. The present disclosure describes devices and methods for achieving at least some of these objectives. Methods and devices described herein are directed towards eliminating potentially harmful contaminants, such as, for example, bacteria, bacteriophages, molds, spores, viruses, and/or other particulates from an enclosed space. Such decontamination is achieved through the generation and release of ozone into the enclosed space. Various embodiments of the devices and methods described herein further provide for accelerated degradation of the ozone upon sterilization in order to quickly return the air in the enclosed space to safe ozone levels.

The embodiments disclosed herein each have several innovative aspects, no single one of which is solely responsible for the desirable attributes mentioned above. Without limiting the scope, as expressed by the claims that follow, the more prominent features will be briefly disclosed here. After considering this discussion, one will understand how the features of the various embodiments provide several advantages over current sterilization devices and methods.

One aspect of the disclosure is a method of sterilizing. In some embodiments, the method includes identifying an environment with an enclosed space. In some embodiments, the method includes placing a portable sterilization unit within the enclosed space. In some embodiments, the sterilization unit includes an ozone generator configured to ozonize air that enters the sterilization unit during an ozone generation cycle, and an ozone degrader configured to remove ozone that enters the sterilization unit during an ozone degradation cycle. In some embodiments, the method includes recording at least one parameter of the ozone generation cycle or the ozone degradation cycle. In some embodiments, the method includes generating a report based in part on the at least one parameter. In some embodiments, the method includes storing the report.

In some embodiments, identifying an environment with an enclosed space further includes reading a RFID tag associated with the environment. In some embodiments, identifying an environment with an enclosed space further includes reading an identifier with a reader of the sterilization unit. In some embodiments, identifying an environment with an enclosed space further includes transmitting a serial number to the sterilization unit. In some embodiments, placing a portable sterilization unit within the enclosed space further includes placing the sterilization unit within an ambulance. In some embodiments, placing a portable sterilization unit within the enclosed space further includes placing the sterilization unit within one vehicle of a fleet of medical response vehicles. In some embodiments, placing a portable sterilization unit within the enclosed space further includes placing the sterilization unit within a helicopter. In some embodiments, the method includes placing the sterilization unit within a second enclosed space of a second environment. In some embodiments, the at least one parameter is selected from the group consisting of: date, start time of the ozone generation cycle, run time of the ozone generation cycle, end time of the ozone generation cycle, start time of the ozone degradation cycle, run time of the ozone degradation cycle, end time of the ozone degradation cycle, and total run time of sterilization unit. In some embodiments, the sterilization unit generates the report. In some embodiments, the sterilization stores the report. In some embodiments, the method includes transmitting the report to a database using a wireless connection. In some embodiments, the database is located on the cloud. In some embodiments, the method includes manually adding information to the report. In some embodiments, the method includes generating alerts based upon at least one report. In some embodiments, the at least one parameter is ozone levels based on an ozone sensor located within the sterilization unit.

Another aspect of the disclosure is an ozone sterilization unit. In some embodiments, the sterilization unit includes a reader configured to read an identifier located within an environment. In some embodiments, the sterilization unit includes an ozone generator configured to ozonize air that enters the sterilization unit during an ozone generation cycle. In some embodiments, the sterilization unit includes an ozone degrader configured to remove ozone that enters the sterilization unit during an ozone degradation cycle. In some embodiments, the sterilization unit is configured to record at least one parameter of the ozone generation cycle or the ozone degradation cycle. In some embodiments, the sterilization unit is configured to generate a report based at least in part on the at least one parameter. In some embodiments, the sterilization unit includes a transmitter configured to send the report.

In some embodiments, the sterilization unit includes an ozone sensor configured to detect the level of ozone within the environment. In some embodiments, the sterilization unit is portable. In some embodiments, the sterilization unit includes a user interface configured to allow a user to input instructions for the ozone generation cycle or ozone degradation cycle.

A further aspect of the disclosure is a sterilization unit for decontaminating an enclosed space. In some embodiments, the sterilization unit includes a first housing defining an ozone generation cavity, a second housing defining an ozone degradation cavity, an ozone generator disposed within the ozone generation cavity and configured to ozonize air that enters the ozone generation cavity, and an ozone degrader disposed within the ozone degradation cavity and configured to remove ozone from air within the ozone degradation cavity. In some such embodiments, the first housing and the second housing are integrated to form a single housing unit. In other embodiments, the first housing and the second housing are physically distinct and/or separated. For example, in one aspect, the first housing and the second housing are not integrated into a single housing unit and are located some distance away from each other. The first housing and the second housing can be located at different locations within the enclosed space to be decontaminated. In some aspects, the sterilization unit includes a first housing and a second housing that are physically located a distance away from each other within the enclosed space, such as but not limited to 1, 2, 3, 4, 6, 8, 10, 12, or more feet from each other. In some embodiments, the first housing and the second housing are physically located a distance away from each other within the enclosed space by a distance of between about 6 inches and about 12 inches. In one non-limiting example, in one embodiment of the sterilization unit, the first housing defining an ozone generation cavity is located near the top of an enclosed space to be decontaminated, while the second housing defining the ozone degradation cavity is located near the base of the enclosed space.

In some embodiments, the sterilization unit further includes a first air-moving component positioned in or next to the ozone generation cavity. The first air-moving component can be configured to move air from the enclosed space into a first inlet, through the ozone generation cavity, and out a first outlet. In some embodiments, the sterilization unit also includes a second air-moving component positioned in or next to the ozone degradation cavity. The second air-moving component can be configured to move air from the enclosed space into a second inlet, through the ozone degradation cavity, and out a second outlet.

In some embodiments, the sterilization unit further includes a processor that controls the ozone generator, the first air-moving component, and the second air-moving component in order to initiate and terminate an ozone generation cycle and an ozone degradation cycle. In some such embodiments, the sterilization unit also includes a user interface configured to receive inputs from a user and send command outputs to the processor. Additionally or alternatively, in some embodiments, the sterilization unit includes a battery to supply power to the sterilization unit.

Some embodiments of the sterilization unit also include a vortex plate positioned within the ozone degradation cavity. The vortex plate is configured to induce at least partially vortical flow of the air passing through the ozone degradation cavity.

A dust filter is disposed in the first inlet of the sterilization unit in some embodiments; in other embodiments, the dust filter is disposed in the ozone generation cavity between the first inlet and the ozone generator. Other embodiments may have no dust filter.

In some embodiments of the sterilization unit, the first and second air-moving components are selected from the group consisting of: a fan and an air blower. In other embodiments, different air-moving components known to one having skill in the art may be used.

The ozone generator of some embodiments is selected from the group consisting of: a corona discharge ozone generator, an ultraviolet ozone generator, and a vacuum-ultraviolet ozone generator. In other embodiments, a different ozone generating device known to one having skill in the art is used. In some embodiments, the ozone generator includes a plurality of ceramic plates with each of the ceramic plates at least partially coated or wrapped with a layer comprising a heavy metal. In some such embodiments, the layer at least partially coating or wrapping around a ceramic plate includes mesh formed of a metal selected from the group consisting of: steel, copper, nickel, cobalt, zinc, iron, silver, gold, and any combination thereof. The ozone generator of some embodiments is configured to produce a gas that includes both ozonized air and heavy metal ions. In some such embodiments, the ozone generator is configured to produce a gas that includes ozonized air and silver ions.

The ozone degrader of some embodiments is selected from the group consisting of: an ozone oxidation catalyst, a catalytic filter, a filter and any combination thereof. In other embodiments, a different ozone degrading device known to one having skill in the art is included in the sterilization unit. In some embodiments, the ozone degrader is formed, at least in part, of activated carbon. The ozone degrader of some embodiments includes a plurality of filters. In some such embodiments, the sterilization unit includes activated carbon-based materials compressed between the plurality of filters.

Another further aspect of the disclosure is a method of decontaminating an enclosed space using any embodiment of the sterilization unit described above. In some embodiments, the method includes moving air containing oxygen from the enclosed space into the ozone generation cavity using a first air-moving component to bring at least some of the air into contact with the ozone generator, converting at least some of the oxygen in the ozone generation cavity into ozone, discharging ozonized air into the enclosed space at least until the enclosed space reaches a measurable ozone concentration, moving the ozonized air from the enclosed space into the ozone degradation cavity using a second air-moving component to bring at least some of the ozonized air into contact with the degrader, converting at least some of the ozonized air into deozonized air, and discharging deozonized air into the enclosed space at least until the enclosed space reaches a safe concentration of ozone.

A further aspect of the disclosure is another method of decontaminating an enclosed space. In some embodiments, the method first includes providing a sterilization unit. The sterilization unit of some such embodiments includes a housing, which defines an ozone generation cavity having a first inlet and first outlet, and an ozone degradation cavity having a second inlet and second outlet, an ozone generator disposed within the ozone generation cavity, a first air-moving component positioned in or next to the ozone generation cavity, an ozone degrader disposed within the ozone degradation cavity, and a second air-moving component positioned in or next to the ozone degradation cavity. Using the provided sterilization unit, the method of some embodiments further includes activating the first air-moving component to move air containing oxygen from the enclosed space into the ozone generation cavity, thereby bringing air into contact with the ozone generator, activating the ozone generator to convert at least some of the oxygen in the ozone generation cavity into ozone, discharging ozonized air into the enclosed space at least until the enclosed space reaches a measurable ozone concentration, activating the second air-moving component to move the ozonized air from the enclosed space into the ozone degradation cavity, thereby bringing the ozonized air into contact with the degrader to produce deozonized air, and discharging deozonized air into the enclosed space at least until the enclosed space reaches a safe concentration of ozone.

In some embodiments of the methods disclosed herein, the measurable ozone concentration is defined as an ozone concentration above 0.1 ppm. In some embodiments, the measurable ozone concentration is defined as an ozone concentration above 0.01 ppm. In some embodiments, the measurable ozone concentration is defined as an ozone concentration above 0.02 ppm. In some embodiments, the measurable ozone concentration is defined as an ozone concentration between about 0.01 to about 0.02 ppm. In some embodiments, the measurable ozone concentration is defined as an ozone concentration between about 0.01 to about 0.1 ppm. Further, in some embodiments disclosed herein, the safe ozone concentration is defined as an ozone concentration below 0.1 ppm. In some embodiments, the safe ozone concentration is defined as an ozone concentration up to 0.2 ppm for no more than 2 hours of exposure. In some embodiments, the safe ozone concentration is defined as an ozone concentration up to 0.1 ppm for 8 hours per day of exposure doing light work. In some embodiments, the safe ozone concentration is defined as an ozone concentration up to 0.08 ppm for 8 hours per day of exposure doing moderate work. In some embodiments, the safe ozone concentration is defined as an ozone concentration up to 0.05 ppm for 8 hours per day of exposure doing heavy work.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. The relative dimensions of the following figures may not be drawn to scale.

FIG. 8 is a report related to a sterilization unit.

DETAILED DESCRIPTION OF CERTAIN EMBODIMENTS

Figure 1:
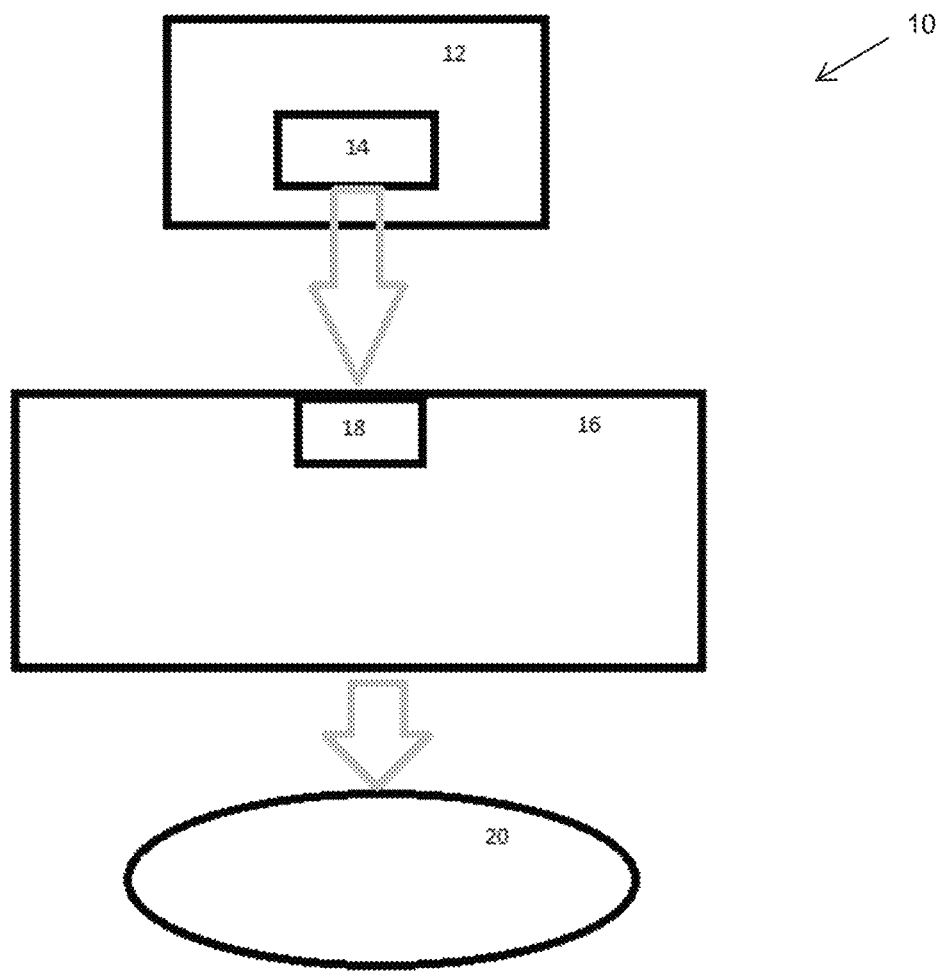
FIG. 1 is an overview of an ozone sterilization system according to implementations described herein.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

The terminology used herein is for the purpose of describing particular embodiments only and is not intended to be limiting of the disclosure. It will be understood by those within the art that if a specific number of a claim element is intended, such intent will be explicitly recited in the claim, and in the absence of such recitation, no such intent is present. For example, as used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises," "comprising," "includes," "including," "haves," and "having," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

To assist in the description of the devices and methods described herein, some relational terms are used. "Connected" and "coupled," and variations thereof, as used herein, include direct connections, such as being contiguously formed with or attached directly to, on, within, etc. another element, as well as indirect connections where one or more elements are disposed between the connected elements. "Connected" and "coupled" may refer to a permanent or non-permanent (i.e., removable) connection. "Secured" and variations thereof as used herein include methods by which an element is directly fastened to another element, such as being glued, screwed or otherwise affixed directly to, on, within, etc. another element, as well as indirect means of securing two elements together where one or more elements are disposed between the secured elements.

A need exists for an effective, safe, convenient, and relatively low-cost sterilization method capable of thoroughly sterilizing an enclosed space. The present disclosure describes devices and methods directed towards eliminating potentially harmful contaminants, such as, for example, bacteria, bacteriophages, molds, and viruses from an enclosed space using ozone. In some embodiments, the contaminants can be selected from one or more of the following: *G. stearothermophilus, B. atrophaeus, B. subtilis, B. anthrax* (and spores), *B. cereus, B. spizizenii, C. difficile, S. aureus, Propionibacterium acnes, S. pyogenes, Acinobacter baumannii, Enterococus faecalis, E. coli, Haemophilus influenzae, Klebsiella pneumoniae, Legionella pneumophila, Pseudomonas aeruginosa, Mycobacterium, smegmatis, S. mutans, S. epidermidis, S.* and *C. pneumoniae, B. anthrasis, C. trachomatis,* Murine Novovirus, Norovirus, Feline calicivirus (FCV), Eurotium (Xerophile), *Cladosporium* spp., *Stachybotrys* spp., and *Aspergillus niger.*

Embodiments of the system 10 and sterilization units 16 described herein can advantageously sterilize an enclosed space with ozone gas by destroying and/or killing contaminants. A partial, nonexhaustive list of contaminants that can be destroyed by embodiments of systems and methods described herein is provided in Appendix A.

Advantageously, ozone is a powerful oxidant known to have a broad spectrum of activity, capable of killing bacteria, bacteriophages, molds, viruses, and fungi and eliminating many odors and environmental particulates. Additionally, ozone is gaseous, and thus, able to flow through ventilation shafts and filters and difficult-to-reach places for thorough sterilization of enclosed spaces. Moreover, ozone is relatively easy to generate from a widely accessible compound—oxygen, and similarly, ozone degrades relatively easily back down to a stable and benign compound—oxygen.

In water, ozone has been shown to be a highly effective disinfectant with a relatively short half-life (of approximately 8-30 minutes); thus, it is commonly used to disinfect swimming pools and water supplies. Ozone is also an effective disinfectant in non-aqueous settings; however, ozone is less frequently used to disinfect the air, because the powerful oxidant has a half-life in the air as long as 36-72 hours. Ozone's oxidative nature makes it toxic to humans. The U.S. Occupational Safety and Health Administration (OSHA) limits acceptable ozone exposure in the workplace to under 0.1 ppm per workday.

Accordingly, various embodiments of the methods and devices disclosed herein provide for: (1) the sterilization of an enclosed space through ozone generation, and (2) accelerated degradation of the ozone upon sterilization. Various embodiments of the methods and devices are automated, allowing for the generation and degradation of ozone with minimal human involvement. Such devices and methods may limit workers' exposure to ozone while also reaching sterilization-achieving ozone levels.

FIG. 1 provides an overview of an ozone sterilization system 10 according to implementations described herein. The system 10 includes one or more environments 12 to be sterilized. The environment 12 can be a medical environment. Each environment can have an enclosed space as described herein. Examples of medical environments include, but are not limited to, ambulances, mobile hospitals, mobile clinics, mobile laboratories, life flight helicopters, urgent and non-urgent vehicles for medical transport, and hospital rooms. The system 10 can include a plurality of environments 12 (e.g., two, three, four, five, six, more than two, more than three, more than four, more than five, more than six). The system 10 can include a fleet of vehicles. Each environment 12 can include a tracker 14. The tracker 14 can include an identifier such as a serial number. The tracker 14 is configured to send the identifier to other components of the system 10. In some embodiments, the tracker 14 only sends information to other components of the system 10. In some embodiments, the tracker 14 can receive information from other components of the system 10. The tracker 14 can store the identifier or other information relevant for a sterilization process performed in the environment 12 by the system 10.

Although the present disclosure describes a system 10 in the context of a plurality of medical environments including a fleet of vehicles, embodiments of the system 10 can be used in various types of environments. For example, in another embodiment, the system 10 includes one or more environments 12 that are pharmaceutical environments, such as laboratory testing facilities or pharmaceutical manufacturing facilities. The system 10 can sterilize a variety of enclosed spaces in the one or more pharmaceutical environments, where the enclosed spaces are of varying sizes and are situated in different locations (such as in different rooms, different buildings, different warehouses, different cities, or different states, for example). Examples of enclosed spaces in the pharmaceutical environments 12 that can be sterilized can include, but are not limited to, clean rooms in a pharmaceutical and/or medical device manufacturing facility and spaces within pieces of equipment used in the manufacture of pharmaceuticals and/or medical devices. The system 10 can sterilize enclosed spaces in other kinds of environments, such as scientific and research environments, including research laboratories and mobile teams responding to reports of disease or contaminant outbreaks. In another non-limiting example, the system 10 can sterilize postal environments, including facilities where mail and packages are collected, sorted, and/or distributed, as well as a fleet of vehicles that deliver mail and packages. Embodiments of the system 10 can also sterilize environments where casualties of chemical, biological, and radiological warfare are decontaminated and/or treated, including military facilities and vehicles (including land vehicles, ships with onboard medical spaces, planes, helicopters, and other military vehicles whether or not their primary mission is medical response and treatment).

As will be described in detail below, embodiments of the system 10 described herein can advantageously track and sterilize environments that include enclosed spaces that move to different locations, as well as generate and send reports regarding sterilization events that have occurred within the environment or that are occurring within the environment in real time. Features of the system 10 are particularly advantageous to coordinate, track, sterilize, and provide reports on multiple mobile elements, such as vehicles, that are sterilized on a regular schedule and/or on demand in response to a contamination or desterilizing event.

Embodiments of the system 10 can include a sterilization unit 16. The sterilization unit 16 can perform the function of reading the tracker 14. The sterilization unit 16 can include a reader 18. The reader 18 can receive information from the tracker 14. For instance, the reader 18 can read the identifier of the tracker 14. The reader 18 can gather any information stored on the tracker 14 including information regarding the environment 12. In some embodiments, the reader 18 can send information to the tracker 14.

The sterilization unit 16 can perform a sterilization process as described herein. The sterilization unit 16 can include a user interface to control aspects of the sterilization process. For instance, the sterilization unit 16 can start the sterilization process when the user enters an input.

The sterilization unit 16 can perform the function of recording information. For example, in some implementations, the sterilization unit 16 can record data generated by the sterilization process. The sterilization unit 16 can generate reports based on the data generated by the sterilization process. The sterilization unit 16 can also perform the function of storing information. For instance, the sterilization unit 16 can store the reports. The sterilization unit 16 can store programs related to the sterilization process. The sterilization unit 16 can store any data, such as any data relevant to or generated by the sterilization process. The sterilization unit 16 can perform the function of generating reports. The reports can be generated from recorded data. The reports can include information stored by the sterilization unit. The reports can include information received by the tracker 14. Additionally, the sterilization unit 16 can transmit information. For instance, the sterilization unit can transmit the reports. The sterilization unit 16 can include hardware and/or software to perform various functions.

The system 10 can include computing resources 20. The sterilization unit 16 can communicate with the computing resources 20. The sterilization unit 16 can send information to the computing resources 20. For instance, the sterilization unit 16 can send information related to the sterilization process such as, but not limited to, run time and ozone levels. The sterilization unit 16 can send the reports created by the sterilization unit 16 to the computing resources 20. The computing resource 20 can be the cloud. The cloud or cloud computing allows network access to shared processing resources. The shared resources can be shared among a plurality of distinct entities or users. The resources can be reallocated among many users. Users can access the cloud using networked devices, such as computers, tablets, and smartphones. The computing resource 20 can include database storage. The computing resource 20 can include computing capabilities. The computing resources 20 can store information.

The computing resources 20 can provide information to a user, such as the reports generated by the sterilization unit 16. The computing resources 20 can include a forward facing interface. The forward facing interface can require a secure login. The forward facing interface can allow the user to enter information related to the sterilization process. The computing resources 20 can include a rear facing interface. The rear facing interface can include alerts for servicing the sterilization unit 16. The rear facing interface can provide back-up for reports generated by the sterilization unit 16.

Figure 2:
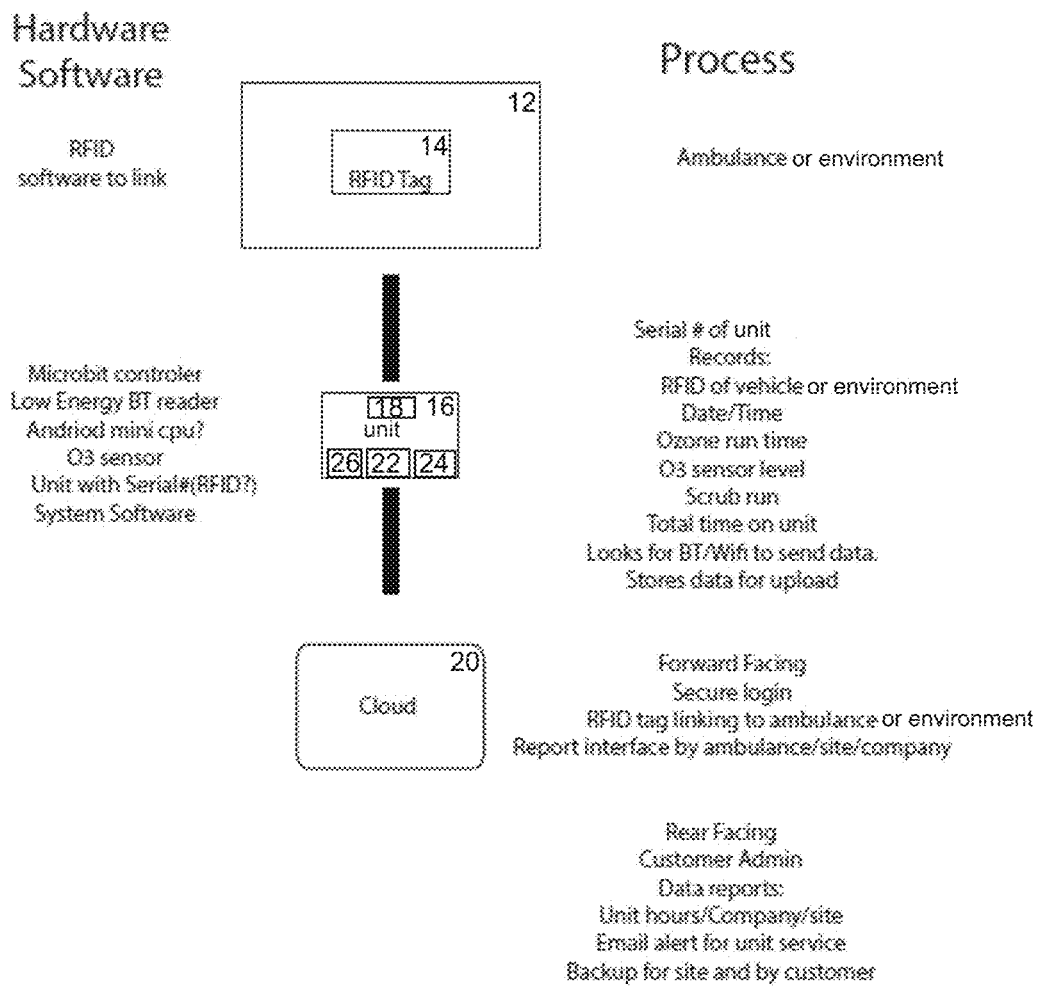
FIG. 2 is one embodiment of the ozone sterilization system of FIG. 1.
Figure 3:
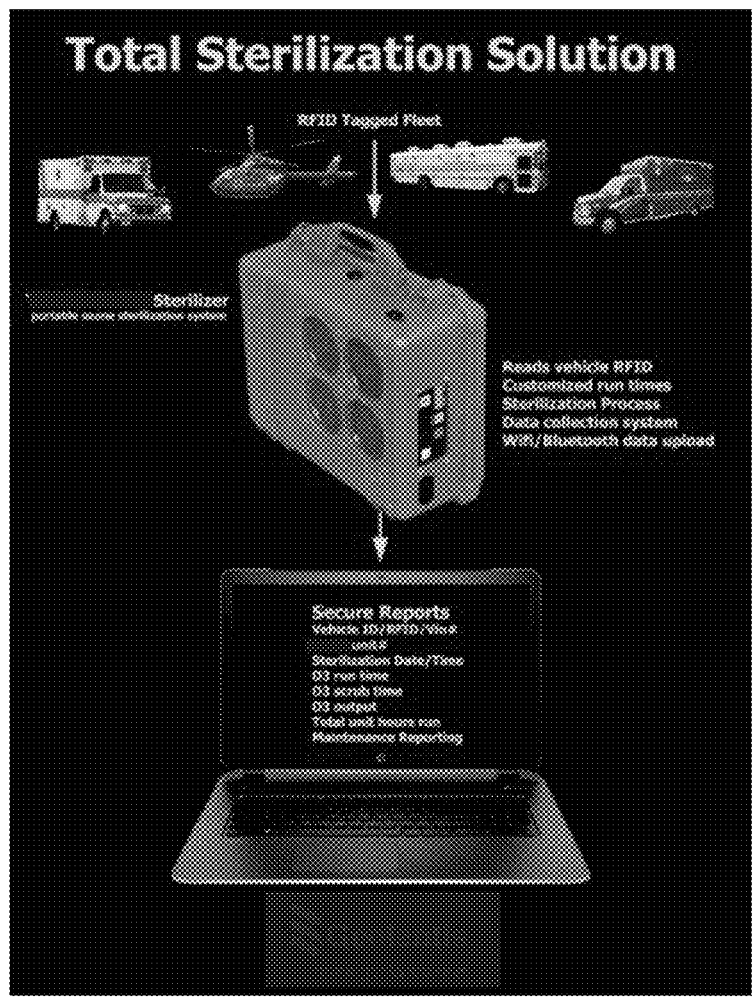
FIG. 3 is another embodiment of the ozone sterilization system of FIG. 1.

FIG. 2 schematically illustrates one embodiment of the ozone sterilization system 10 of FIG. 1. The system 10 shows one environment 12 but, as described above, embodiments of the system 10 can advantageously include more than one environment. The environment 12 in this non-limiting embodiment is the rear compartment of an ambulance. Although not illustrated, the system 10 can include a plurality of environments 12, for example an ambulance fleet including a plurality of ambulances. The system can also include other types of environments 12 such as one or more mobile hospitals, mobile clinics, mobile laboratories, life flight helicopters, urgent and non-urgent vehicles for medical transport, and hospital rooms. The system 10 can sterilize one or more enclosed spaces in a medical system that includes the various environments 12 in the system 10. In one non-limiting implementation, the system 10 can sterilize a fleet of first responder vehicles. For example, the system 10 can sterilize ambulances, emergency response helicopters, and medical spaces (such as hospital rooms, clinics, mobile laboratories, etc.) in a medical system. FIG. 3 shows an example of a fleet of vehicles in a medical system that can be sterilized by the system 10.

In some cases, the system 10 can sterilize a medical system that includes medical facilities and vehicles within one geographic region, such as a geographical district in a city serviced by a particular hospital. In other cases, the medical system sterilized by the system 10 includes medical facilities and vehicles within a group that is not defined by a geographic region, for example a group that is defined by business considerations or other parameters, such as a group of medical facilities and vehicles that are insured by a common insurance provider. The medical system sterilized by the system 10 can include medical facilities and vehicles within a group defined by a combination of parameters. In one non-limiting example, the combination of parameters includes proximity to a central sterilization location, frequency of use of the medical facility and vehicles, and proximity in time and/or location to a contamination event.

Each environment 12 can have a tracker 14. The tracker 14 can store an identifier such as a serial number which identifies the tracker 14. In other embodiments, the tracker 14 can store information which identifies the environment 12. For example, the stored information can include the VIN number of the vehicle, license plate of the vehicle, company that owns, services, and/or uses the vehicle, and/or the make or model of the vehicle. The stored information can identify company specific information regarding the environment 12. For example, the stored information can include a company-assigned number to the vehicle, the shifts associated with the vehicle, and the drivers associated with the vehicle. The stored information can identify a parameter of the environment 12. For example, the stored information can include the volume of the enclosed space of the environment 12.

In some embodiments, the tracker 14 can include a Radio-frequency identification (RFID) tag. A RFID tag uses radio frequency to transfer information. A RFID tag includes a circuit for storing and/or processing information and an antenna for receiving and transmitting the RF signal. In some embodiments, the RFID tag can be embedded or otherwise located within the environment 12. A RFID tag can store information such as identifying information for the object to which the RFID tag is attached.

In some embodiments, the tracker 14 can be read-only. The tracker 14 can have an assigned serial number or other identifier that is used as an input to the reader 18. In some embodiments, the tracker 14 can include environment specific data. This data can be programmable once or multiple times.

In some embodiments, the tracker 14 is a bar code. The bar code requires a line of sight between the reader 18 and the barcode. In some embodiments, the tracker 14 is a sign. The sign requires a line of sight between the reader 18 and the sign. In other embodiments, the tracker 14 does not require a line of sight between the tracker 14 and the reader 18.

The tracker 14 can be affixed or otherwise mounted in the environment 12. The tracker 14 can be permanently attached to the environment 12 such as through an adhesive. The tracker 14 can be removable from the environment 12. The tracker 14 can be removed from one environment and attached to another environment based on the needs of the user. The user can place the tracker 14 within the environment.

The tracker 14 can function to transfer data for the purposes of identifying the tracker 14 or the environment 12. In some embodiments, the reader 18 and the tracker 14 have two-way communication transmission to allow each to send and receive a signal. The reader 18 can send a signal to the tracker 14 and the tracker 14 can receive the signal. The tracker 14 can send a signal to the reader 18 and the reader 18 can receive the signal. In some cases, the tracker 14 receives a signal from the reader 18 and then responds with information such as an identifier.

Each tracker 14 can have a unique identifier. The reader 18 can discriminate among several trackers 14 that might be within a detection range of the reader 18. In some embodiments, the tracker 14 transmits an identifier and information regarding the environment 12 to the reader 18. For instance, the tracker 12 can identify a characteristic of the environment such as the cubic volume of the enclosed space. Each tracker 14 can transmit one or more types of identifying information.

The system 10 can include the reader 18. The reader 18 is configured to receive the information from the tracker 14. For instance, the reader 18 is configured to receive the unique identifier of the tracker 14. The reader 18 can transmit this information to other hardware or software of the sterilization unit 16. The reader 18 can allow the sterilization unit 16 to identify an environment 12 including an enclosed space within which the sterilization unit 16 is placed.

The type of reader 18 included in sterilization unit 16 can depend on the type of tracker 14 included in the environment(s) 12 of the system 10. As noted above, the tracker 14 can be a RFID tag. RFID tags can be active, passive or battery-assisted passive. An active RFID tag is connected to a battery and periodically transmits a signal. An active RFID tag can be used with a Passive Reader Active Tag (PRAT) system, which has a passive reader and one or more active tags. An active RFID tag can be used with an Active Reader Active Tag (ARAT) system, which has both an active reader and one or more active tags or battery-assisted passive tags. A passive RFID tag relies on radio energy transmitted by the reader 18. A passive RFID tag can be used with an Active Reader Passive Tag (ARPT) system which has an active reader and one or more passive tags.

The system 10 can include the sterilization unit 16. The sterilization unit can perform the function of reading the tracker 14. In some embodiments, the reader 18 is embedded or attached to the sterilization unit 16. In other embodiments, the reader 18 is coupled to the sterilization unit 16 such as in a removable fashion. The reader 18 can be in communication with other hardware or software of the sterilization unit 16. The reader 18 can relay the identifier of tracker 14 to other components of the sterilization unit 16.

The system 10 deploys a portable, ruggedized sterilization unit 16. FIG. 3 shows an embodiment of the ruggedized sterilization unit 16. One non-limiting example a sterilization unit 16 described herein is the Ozilla® EMS Sterilizer produced by Genlantis. The sterilization unit 16 can be placed within environment 12. The sterilization unit 16 can have an outer housing configured for placement within an environment 12. In some embodiments, the sterilization unit 16 is a portable unit having features to facilitate movement of the unit. For example, the sterilization unit 16 can be small in size to allow for the sterilization unit 16 to be easily placed within the environment 12 (e.g. small volume, less than 500 in$^3$, less than 400 in$^3$, less than 300 in$^3$, less than 200 in$^3$, less than 100 in$^3$, etc). For example, the sterilization unit 16 can be lightweight to be lifted by a person (e.g., 50 pounds, 40 pounds, 30 pounds, 20 pounds, 10 pounds, less than 50 pounds, less than 40 pounds, less than 30 pounds, less than 20 pounds, less than 10 pounds, etc.). The sterilization unit 16 can include a handle to facilitate portability. The sterilization can be placed within the environment 12 and removed from the environment 12. In other embodiments, the sterilization unit 16 is a semi-permanent or fully permanent fixture within the environment 12.

The sterilization unit 16 can be an ozone generation and degradation unit. The sterilization unit 16 can rapidly sterilize enclosed spaces, such as enclosed spaces associated with medical transport. The sterilization unit 16 can include any of the features of sterilization units described below. The sterilization unit 16 is configured to sterilize an enclosed space by generating the powerful oxidant, ozone, and releasing the ozone into the enclosed space. In some embodiments, the enclosed space is air-tight. The enclosed space can be impervious to outside gases. The ozone generated by the sterilization unit 16 can be entirely contained within the enclosed space. In other embodiments, the enclosed space is not air-tight. The enclosed space can include doors or windows which do not fully seal in gases. In some embodiments, the enclosed space may be substantially but not fully air-tight, such as, for example, a passenger area of an ambulance.

In various embodiments, the sterilization unit 16 generates ozone during an ozone generation cycle. In such a cycle, air is guided from the enclosed space into the sterilization unit 16 and into an ozone generation cavity where oxygen in the air is converted to ozone. The ozonized air is then dispelled out of the sterilization unit 16 back into the enclosed space. The oxidative and reactive ozone in the air has a sterilizing effect within the enclosed space. An ozone generation cycle may continue for a specific amount of time or until a specific ozone concentration is reached within the enclosed space.

The sterilization unit 16 can accelerate ozone degradation in the enclosed space. During ozone degradation, the oxidative and reactive ozone is broken down to the stable and safe compound, oxygen. The sterilization unit 16 accelerates ozone degradation at least during an ozone degradation cycle once sterilization is complete. In such a cycle, ozonized air is guided from the enclosed space through the sterilization unit 16 and into an ozone degradation cavity where the ozone in the air is converted back to a stable oxygen molecule. The de-ozonized air is then dispelled out of the sterilization unit 16 back into the enclosed space. Through this ozone degradation cycle, ozone is removed from the air, thereby making the air safe for human exposure.

The sterilization unit 16 can generate ozone during an ozone generation cycle that varies in time according to characteristics of the enclosed space to be sterilized. In some cases, the length of time of the ozone generation cycle is determined by the volume of the enclosed space in which the sterilization unit 16 is placed. In another case, the length of time of the ozone generation cycle is determined by a defined time by which the enclosed space (such as an enclosed space in an ambulance) is required to be back in service in a fleet of ambulances.

Additionally, the sterilization unit 16 can generate ozone during an ozone generation cycle that varies in time according to other parameters that are not related to the characteristics of the enclosed space to be sterilized. In one non-limiting example, the length of time of the ozone generation cycle is determined by a particular pathogen or contaminant that a user suspects (or has confirmed) exists in the enclosed space. In still other cases, the sterilization unit 16 can generate ozone during an ozone generation cycle that varies in time according to a combination of parameters or characteristics. In one implementation, a maximum-length ozone generation cycle is determined based on a plurality of pathogens or contaminants (for example, pathogen A, contaminant B, and pathogen C) that are likely to exist in a plurality of enclosed spaces, such that all of the enclosed spaces are sterilized by the sterilization unit 16 for the maximum-length ozone generation cycle. This can ensure or increase the likelihood that all of the plurality of pathogens or contaminants (in this example, pathogen A, contaminant B, and pathogen C) will not be present in the enclosed spaces in the environment(s) 12 following sterilization with the sterilization unit 16.

The length of time of the ozone degradation cycle can also vary based on one or more characteristics or parameters. For example, in one case, the length of time of the ozone degradation cycle can be based on the volume of the enclosed space in which the sterilization unit 16 is placed. In another example, the length of time of the ozone degradation cycle can be determined based on safety considerations, for example the proximity of the enclosed space to other enclosed spaces, buildings, foot or vehicular traffic, or living beings such as humans and animals.

In still another example, a maximum-length ozone degradation cycle is determined based on a minimum amount of time that is required for ozonized air in all of a plurality of enclosed spaces to be removed or decreased to a level that is safe for human exposure. In one instance, a first enclosed space A may require an ozone degradation cycle time of 1 hour for air in the first enclosed space A to return to a level that is safe for human exposure. A second enclosed space A may require an ozone degradation cycle time of 1 hour 30 minutes for air in the second enclosed space B to return to a level that is safe for human exposure. A third enclosed space C may require an ozone degradation cycle time of 45 minutes for air in the third enclosed space C to return to a level that is safe for human exposure. In this example, the minimum amount of time that is required for ozonized air in all of enclosed spaces A, B, and C to be removed or decreased to a level that is safe for human exposure is 1 hour 30 minutes. A maximum-length ozone degradation cycle time of 1 hour 30 minutes can be established based on this parameter, such that the sterilization unit 16 will use an ozone degradation cycle time of 1 hour, 30 minutes during each sterilization process for first enclosed space A, second enclosed space B, and third enclosed space C.

In some embodiments, the ozone generation cycle is 3 hours, 2 hours, 1 hour, 45 minutes, 30 minutes, 15 minutes, less than 3 hours, less than 2 hours, less than 1 hour, less than 45 minutes, less than 30 minutes, less than 15 minutes. In some embodiments, the ozone degradation cycle is 3 hours, 2 hours, 1 hour, 45 minutes, 30 minutes, 15 minutes, less than 3 hours, less than 2 hours, less than 1 hour, less than 45 minutes, less than 30 minutes, less than 15 minutes. In some embodiments, the total sterilization process including ozone generation and ozone degradation is 3 hours, 2 hours, 1 hour, 45 minutes, 30 minutes, 15 minutes, less than 3 hours, less than 2 hours, less than 1 hour, less than 45 minutes, less than 30 minutes, less than 15 minutes. In some embodiments, the ozone degradation cycle immediately follows the ozone generation cycle. In other embodiments, there is a period of time between the ozone degradation cycle and the ozone generation cycle. In some embodiments, there is an automatic and accelerated conversion of ozone back to oxygen by the sterilization unit 16.

The sterilization unit 16 can be pre-programmed for a particular ozone generation cycle, ozone degradation cycle, and total sterilization process time. As will be described in detail below, in some cases, the sterilization unit 16 includes a user interface that allows a user to enter a particular ozone generation cycle, ozone degradation cycle, and total sterilization process time based on the enclosed space in which the sterilization unit 16 is placed. Advantageously, embodiments of the sterilization unit 16 described herein can be programmed remotely to implement a particular ozone generation cycle, ozone degradation cycle, and total sterilization process time. For example, information on a particular ozone generation cycle, ozone degradation cycle, and total sterilization process time can be transmitted to a CPU (described in detail below) in the sterilization unit 16. Accordingly, implementations of sterilization units 16 described herein can be programmed either manually or remotely.

Optional safety measures can also be implemented in sterilization units 16 described herein. For example, sterilization units 16 that can be programmed remotely may also display or announce safety prompts. The safety prompts may be a visual signal or indicator displayed to the user on the user interface, or any other suitable safety prompt, such as an audio or tactile signal. The safety prompt may ask the user, before each run, to agree to having read safety instructions prior to operating the sterilization unit 16. The safety prompt may ask the user, before each run, to confirm completion of safety measures (such as but not limited to reading safety instructions) by checking a box on the user interface, by verbally confirming completion, or by another suitable method to confirm completion of safety measures. Still other safety measures are possible and can be implemented in embodiments described herein. In one non-limiting example, the sterilization unit 16 can only be activated to begin a sterilization process by a user physically inputting a command to activate the sterilization unit at the user interface (for example, by pressing a "start" button on the user interface).

The sterilization unit 16 can include any hardware and/or software to send and receive information. In some embodiments, the sterilization unit 16 includes WiFi or Bluetooth capabilities. The WiFi or Bluetooth capabilities can send information from the sterilization unit 16. The WiFi or Bluetooth capabilities can receive information from other components of the system 10 or from components outside of the system 10.

The sterilization unit 16 can include a feature to facilitate placement within the environment 12. For instance, a handle can enhance portability and allow for the sterilization unit 16 to hang within an enclosed space. In some embodiments, the environment 12 such as the passenger compartment of an ambulance includes a hook or other mount for the sterilization unit 16. The user can place the sterilization unit 16 within the environment 12 to allow air flow through any air vents or other necessary air pathways. The sterilization unit 16 can include a power cord to connect to an electrical outlet. In other embodiments, the sterilization unit can include a battery.

In some embodiments, ozone generation and ozone degradation occur within separate cavities within an integrated unit. The ozone generation occurs within an ozone generation cavity and ozone degradation occurs within an ozone degradation cavity. While air flow through the ozone generation cavity and ozone degradation cavity is separated, the two cavities can be contained within the same outer housing. Thus, in some aspects, sterilization units described herein include an outer housing enclosing a first housing and a second housing, the first housing including an ozone generation cavity and the second housing including an ozone degradation cavity.

The sterilization unit 16 can include one or more sensors. In some embodiments, the sensors can be located within the outer housing, within the first housing, or within the second housing. The sensors can include an ozone sensor. The ozone sensor can determine a level of ozone in the enclosed space during sterilization. The ozone sensor can detect whether the sterilization unit 16 is functioning properly. For instance, the ozone sensor can detect that the sterilization unit 16 failed to produce ozone or failed to produce sufficient ozone to sterilize the enclosed space. The ozone sensor can produce data over the ozone generation cycle and/or ozone degradation cycle. The ozone sensor can detect ozone at regular intervals during the sterilization process. In some embodiments, the user can determine the intervals to detect ozone. In one example, the user can pre-program the sterilization unit 16 to detect ozone at particular intervals prior to the start of the sterilization process (where the "sterilization process" in this example begins at the start of the ozone generation cycle and ends at the end of the ozone degradation cycle). Additionally, the user can remotely change the detection interval (or any other parameter of the sterilization process) "on-the-fly" while the sterilization process is occurring, for example by sending information to a CPU of the sterilization unit using WiFi, Bluetooth, or other suitable communication networks.

Embodiments of sterilization units 16 described herein can also include additional advantageous features. In one non-limiting embodiment, the sterilization unit 16 can delay an ozone degradation (or "scrub") cycle a specified amount of time that is inputted by the user. The time during which the start of the ozone degradation cycle is delayed (a "wait" time or "wait" cycle) may be pre-programmed by the user before the sterilization process begins, or it may be remotely programmed in the sterilization unit 16 by the user during the sterilization process. In one non-limiting example where a delayed ozone degradation cycle is remotely triggered by the user, the user initially pre-programs the sterilization unit 16 to execute a 1-hour ozone generation cycle, followed by a 1-hour ozone degradation cycle. During the sterilization process, the user determines that the ozone gas in the enclosed space should remain at a higher concentration than originally planned (or that it would be helpful or beneficial if the ozone gas remained at a higher concentration or remained in the enclosed space for a longer period of time than originally planned). The user may make this determination during the sterilization process based on information collected by sensors in the sterilization unit 16 and transmitted to computing resources 20. To achieve the newly-determined optimal ozone concentration, the user remotely programs the sterilization unit 16 to delay the start of the 1-hour ozone degradation cycle by one hour. Thus, in this non-limiting example, the sterilization unit 16 executes a 1-hour ozone generation cycle, a 1-hour "wait" cycle remotely programmed by the user elapses, then the sterilization unit 16 triggers the delayed start of the 1-hour ozone degradation cycle.

In some embodiments, the ozone sensor can detect ozone continuously. The sterilization unit 16 can be equipped with one or more sensors configured to detect the humidity, pressure, temperature, and/or current ozone level in the enclosed space. The information from one or more sensors can be recorded by the sterilization unit 16, as described herein.

The sterilization unit 16 can include additional software or hardware to interact with the system 10. The sterilization unit 16 can include a central processing unit (CPU). The central processing unit is hardware that executes a program. The sterilization unit 16 can include a control unit which directs the operation of the processor. The sterilization unit 16 can include a microprocessor. The sterilization unit 16 can include a word processor for generating reports. The sterilization unit 16 can include data storage devices or memory to store programs or information.

The sterilization unit 16 can record information. The sterilization unit 16 can include one or more data storage devices 22 which can record information. The data storage device 22 can record an identification of the sterilization unit 16. For instance, the sterilization unit 16 may include one or more sterilization trackers 24 such as a RFID tracker described herein. The sterilization tracker 24 can identify the sterilization unit 16. For example, the tracker 24 can include various kinds of information, such as but not limited to a serial number of the sterilization unit, a make or model of the sterilization unit, and an owner or operating service of the sterilization unit. The tracker 24 can identify company specific information regarding the sterilization unit 16. For example, the stored information can include a company-assigned number of the sterilization unit. The tracker 24 can identify a parameter of the sterilization unit 16. For example, the tracker 24 can include the size of the sterilization unit and a rate of ozone generation (such as the maximum rate of ozone generation of which the sterilization unit is capable). The stored information of the sterilization tracker 24 can be read by the reader 18 or another reader of the sterilization unit 16.

The data storage device 22 can record information from the tracker 14. The data storage device 22 can gather information regarding the environment 12. The sterilization unit 16 can include one or more sensors 26. The one or more sensors 26 can include an ozone sensor. The sterilization unit 16 can be equipped with one or more sensors 26 configured to detect the humidity, pressure, temperature, and/or current ozone level in the enclosed space. The data storage device 22 can record information from one or more sensors 26.

The data storage device 22 can record different types of information. For example, the data storage device 22 can record a date, time, or location. The data storage device 22 can record parameters of the ozone generation cycle. The data storage device 22 can record parameters of the ozone degradation cycle. Examples of parameters of the cycles include but are not limited to start time, end time, duration, ozone levels, peak ozone levels, and interruptions. The data storage device 22 can record parameters related to the sterilization unit 16. Examples of parameters include but are not limited to a total run time of the sterilization unit within an environment, a total time within an environment, a total downtime of the sterilization unit, a transportation time of the sterilization unit, and a total life-time run time of the sterilization unit since it was first placed in use in the system 10.

The sterilization unit 16 can generate reports. The reports can characterize performance of the sterilization unit 16, including cycle start time, cycle end time, cycle duration, ozone levels, peak ozone levels, total run time of the sterilization unit, total time within an environment, total downtime of the sterilization unit, and transportation time of the sterilization unit. The reports can include identification of system 10 including the environment 12, tracker 14, sterilization unit 16, reader 18, and sterilization tracker 24. The reports can include other information including the company-specific information. The reports can be generated based on recorded data. The reports include information stored by the sterilization unit 16. The reports can include data from one or more sensors 26. The reports can track the ozone generation with the ozone sensor. The reports can track other parameters with the one or more sensors 26 of the sterilization unit 16.

The reports can include any type of presentation of data. The reports can include tables of recorded data. The reports can include graphical representations of recorded data. The reports can aggregate data from one or more ozone generation cycles. The reports can aggregate data from one or more ozone degradation cycles. The reports can aggregate data for all cycles of a particular sterilization unit 16. The reports can include any or all data generated by the sterilization process. The reports can include information stored by the data storage devices 22. The reports can include information acquired by the reader 18, such as information from the tracker 14 and/or the sterilization tracker 24.

The sterilization unit 16 can store information. The sterilization unit 16 can include one or more data storage devices 22 which can store information. The data can be stored on a hard drive, flash drive, or other permanent medium. A data may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. In some embodiments, a storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

The sterilization unit 16 can relay information to additional components of the system 10, such as the computing resources 20. The data storage device 22 can temporarily store information until a connection is formed with the computing resources 20. In some embodiments, the sterilization unit 16 can include a communication device for relaying information to the computing resources 20. The communication device can search for a transmission path to send data. The transmission path can be wireless, wired, Bluetooth, WiFi, radiofrequency, etc. The sterilization unit 16 can store data until the sterilization unit 16 can transmit the data. In some embodiments, the sterilization unit 16 records and stores the data even after transmission. In other embodiments, the sterilization unit 16 deletes the stored copy of the data after transmitting the data. In still other embodiments, the sterilization unit 16 deletes data at regular intervals (e.g., after three months, after six months, after one year, after two years).

The sterilization system 16 can include software or hardware to perform one or more of the following functions. The hardware and/or software can send or receive information from the tracker 14. The hardware and/or software can run the ozone generation cycle and/or the ozone degradation cycle. The hardware and/or software can record data such as data from the ozone generation cycle and/or the ozone degradation cycle. The hardware and/or software can generate a report based, at least in part, on the recorded data. The hardware and/or software can store the data and/or the report. The hardware and/or software can transmit the data and/or the report. The hardware and/or software can be in communication with other components of the system 10.

The sterilization can be completed on a regular maintenance schedule or on demand. For instance, an enclosed space (such as but not limited to the passenger compartment of an ambulance) can be sterilized on a regular schedule (e.g., after each shift, once per day, once per week, once per month, bi-monthly, yearly). For instance, an enclosed space (such as but not limited to the passenger compartment of a helicopter) can be performed on demand (e.g., after each patient, after each patient with certain characteristics, after each incident of hospital-acquired infection).

Numerous attributes of the sterilization unit 16 can be controlled by a user through a user interface. The user may be required to be physically present to run the ozone generation cycle. The user can program parameters of the ozone generation cycle and/or the ozone degradation cycle. Examples of parameters of the cycles include fan speed, ozone generation intensity, length of ozone generation and/or ozone degradation cycles, start time of ozone generation and/or ozone degradation cycles, and end time of ozone generation and/or ozone degradation cycles. The sterilization unit 16 can store these programs with the data storage device 22. In some embodiments, the user can input the date and time. In other embodiments, an internal clock in the sterilization unit 16 determines the date and time. In some embodiments, the user can input the ozone run time. In other embodiments, the sterilization unit 16 determines the run time based upon stored information or information from the tracker 14, for instance the volume of the enclosed space or the desired peak ozone level. In some embodiments, the user enters the volume of the enclosed space. In other embodiments, the sterilization unit 16 determines the volume of the enclosed space by stored information or information from the tracker 14. In some embodiments, the user enters the peak ozone concentration the user wishes to achieve within the enclosed space. In other embodiments, the sterilization unit 16 runs a program with a pre-determined peak ozone concentration. The sterilization unit 16 can customize the sterilization process based on user inputs.

The user interface is coupled to the sterilization unit 16 such as within the housing of the sterilization unit 16. The user interface can be an integrated control panel disposed on the sterilization unit 16. In other embodiments, the user interface is positioned on a separately located control panel, a remote control, or other device in wired or wireless communication with the sterilization unit 16. For example, in some embodiments, the sterilization unit 16 is controllable through a user's cell phone or computer. In such embodiments, commands are sent to the sterilization unit 16 from a remote user interface via radiofrequency, WiFi, Bluetooth, and/or near-field communications. The remote user interface may be positioned outside of the enclosed space while the remainder of the sterilization unit is disposed within the space. The user interface can control the sterilization unit 16 remotely.

The user interface can include a touchscreen, physical buttons, keys, knobs, and/or any other input elements that are suitable for manipulating the settings of the sterilization unit 16. In addition to receiving inputs from a user, the user interface can display outputs. The user interface of various embodiments includes one or more lights, visible messages and/or audible alarms to provide users with information about the status of the sterilization unit 16.

The system 10 can include the computing resources 20. The computing resources 20 can receive information from the sterilization unit 16. For instance, the computing resources can receive the reports generated by the sterilization unit 16. FIG. 3 shows a computer connected to the computing resources 20. The computer can display data and/or reports stored by the computing resources 20.

The computing resources 20 can include a forward facing interface. The forward facing interface can require a secure login. In some embodiments, information from the reports is password protected. The user may need to input information that is associated with company employees, for instance a user name or email address. The user may need to input information related to the system 10 to access the computing resources such as information related to the environment 12, the tracker 14, the sterilization unit 16, the reader 18, or any other component of the system 10. In some cases, the user may be required to input information related to the system 10 in order to activate the sterilization unit 16.

The forward facing interface can allow a user to enter information once access to the system 10, or elements of the system 10, is granted. The user can enter the identifier of the tracker 14. For instance, the user can assign the serial number or other identifier to the tracker 14. In some methods of use, the user will enter information related to the environment 12. For instance, the user can enter the VIN number of the vehicle having an enclosed space to be sterilized, license plate of the vehicle, company of the vehicle, and make or model of the vehicle. The user can link the information of the environment 12 to the tracker 14. For instance, reports associated with a unique tracker 14 will identify the unique ambulance in which the tracker 14 is placed. In some methods of use, the user will enter company-specific information. For example, the user can enter the company-assigned number to the vehicle, the shifts associated with the vehicle, and the drivers associated with the vehicle. The user can link the company-specific information to the tracker 14. The user can identify a parameter of the environment 12. For example, the user can identify the volume of the enclosed space of the environment 12. The user can link the parameter to the tracker 14. The user can also enter information related to the sterilization unit 16 using the forward facing interface. For example, the user can enter the identifier of the sterilization tracker 24. For instance, the user can assign the serial number or other identifier to the sterilization tracker 24 using the forward facing interface.

The user-entered information can be incorporated into the report generated by the sterilization unit 16. For instance, identifying information regarding the environment 12 can be displayed on the report. For instance, identifying information such as the company or driver can be displayed on the report. In some embodiments, the user can only add information to the report. In some embodiments, the user cannot alter the data of the report generated by the sterilization unit. For instance, the user cannot alter the date or time, the run time, the peak ozone generation etc.

The user can aggregate data of two or more reports. For instance, reports generated by the sterilization unit 16 can be grouped based on the environment 12, the sterilization unit 16, and the company. The reports generated can be grouped based on the date and time of the sterilization process. The user can select the reports to be aggregated. The user can select parameters to identify reports to be aggregated.

In some embodiments, the user can enter information using an application for mobile devices such as, for example, a mobile "app." The app can utilize features such as a camera to capture information. For instance, the camera can photograph the license plate or VIN number of the vehicle and convert the image into the corresponding series of letters and/or numbers. The app can record time and location of the user. The app can be linked with the user interface to determine information inputted by the user. The app can interact with the sterilization unit 16 and/or the computing resources 20.

The computing resources 20 can include a rear facing interface. The rear facing interface can include alerts for servicing the sterilization unit 16. The computing resources 20 can provide alerts related to the system 10. The alerts can be related to system maintenance. The alerts can be related to parameters of the system such as interruptions and peak ozone levels. The alerts can be based upon total run time of the sterilization unit 16. The computing resources 20 can track the number of hours that sterilization unit 16 is in operation and calculate a regular maintenance schedule. The computing resources 20 can detect outliers in the reports such as low ozone production from the ozone sensor. The computing resources 20 can alert the user to system malfunctions.

The computing resources 20 can provide a duplicate copy or backup of information stored with the data storage device 22. The computing resources 20 can provide real-time backup of information. For instance, the sterilization unit 16 can send data in real-time to the computing resources 20 through a transmission path, such as a Bluetooth or WiFi connection. The rear facing interface can provide backup for data and/or reports generated by the sterilization unit 16.

In some embodiments, the sterilization unit 16 only sends information to the computing resources 20. In other embodiments, the sterilization unit 16 sends and receives information from the computing resources 20.

The system 10 can generate secure reports. The reports can be produced without human intervention. For instance, the reports are generated automatically based on data recorded by the sterilization unit. In some embodiments, the user can enter additional information, such as additional identifying information but cannot alter the content of the report. The report is written evidence of sterilization events. The report verifies that a sterilization event occurred. The report links the sterilization event to the environment 12 which was sterilized. The report links the sterilization event to the sterilization unit 16 which performed the sterilization. The report provides data of the sterilization event such as verifying that peak ozone was achieved. The reports can be used by third parties. The report can be useful for third parties (for example, entities that do not own, use, or service the system 10), such as but not limited to insurance companies evaluating malpractice claims relating to infectious diseases, entities involved in detecting, tracking, and coordinating responses to infectious disease events or outbreaks, entities involved in legal disputes (such as government, public, or private parties), military or law enforcement agencies, or any other third party. The reports can be useful for advertising and sales presentations. The reports can be used to show best practices or standard of care.

The system 10 has additional benefits. The system 10 can reduce vehicle down-time for sterilization. For instance, the sterilization unit 16 can rapidly sterilize an enclosed space. The system 10 can coordinate the placement of a limited number of sterilization units 16 within a fleet of vehicles. The system 10 can coordinate schedules for where and when the sterilization unit 16 should be placed within a certain environment. The system 10 can advantageously optimize movement of a single sterilization unit 16 or a limited number of sterilization units 16 (2, 3, 4, 5, 6, 7, 8, 9, 10, 20, or more) within the system 10 to place the sterilization unit(s) 16 in a plurality of environments 12 rapidly, efficiently, and securely, so that a plurality of facilities and vehicles with enclosed spaces are safely sterilized on a regular schedule, on demand, or both.

The system 10 can ensure safe use of highly toxic ozone gas during sterilization. The system 10 can include an ozone sensor to detect the level of ozone within the enclosed space. The system 10 can produce reports regarding the effectiveness of the sterilization unit 16. The system 10 can ensure proper maintenance based on aggregate data of the run time of the sterilization unit.

The system 10 can track all time, including vehicle down time. The reports can inform better allocation of resources, such as better allocation of a single sterilization unit 16 within a plurality of environments.

The system 10 can store the data on multiple devices or within the cloud. The system 10 can back-up data. The system 10 can store data within the sterilization unit 16. The system can store data within the computing resources 20. The system 10 can store data indefinitely. The system 10 can store data continuously. The system 10 can produce reports to verify that sterilization events occurred and that peak ozone levels were achieved.

The system 10 can destroy pathogens, such as known or unknown infectious diseases or germs. Emergency Medical Services (EMS) providers play an important role in the prevention and control of infections. EMS providers are at the front line of medical care and have a high risk of exposure to patients with known or unknown infectious diseases. The emergence of antimicrobial-resistant bacteria such as methicillin resistant *Staphylococcus aureus* (MRSA) and vancomycin-resistant *enterococcus* (VRE), along with growing concerns regarding the spread of *Clostridium difficile* (*C. diff*) and viruses, are major problems facing all healthcare providers, including EMS providers.

Embodiments of the system 10 and the sterilization units 16 described herein provide a safer and easier way to use ozone gas for multiple sterilization applications. The sterilization unit 16 can be used in various medical environments, including ambulances. The sterilization unit 16 uses ozone generation to sterilize. The sterilization unit 16 can include a special filter to convert ozone gas back to oxygen in minutes after the ozone generation cycle completes.

Embodiments of sterilization units 16 described herein provide a powerful sterilizing effect. The sterilization unit 16 is capable of killing 99.999% of 650 different kinds of pathogenic organisms (bacteria, virus and fungi) in 60 minutes. The sterilization unit 16 is safe and efficient. Embodiments of the sterilization unit 16 described herein do not use any liquids, harmful UV rays, harsh chemicals, or heat. Further, the sterilization unit 16 does not damage surfaces. The sterilization unit 16 provides a complete clean and does not leave any chemical residues behind.

Embodiments of sterilization units 16 described herein have many advantages. The sterilization unit 16 can achieve very high ozone concentration levels and also degrade ozone at an accelerated rate in order to quickly return the air in an enclosed space to a safe ozone level. In one non-limiting example, a system 10 includes a sterilization unit 16 in an environment 12 with an enclosed space that is a small equipment enclosure. The enclosed space in this example is an incubator. The sterilization unit 16 achieves an ozone level of about 400 ppm during the ozone generation cycle. Within 3 minutes of the start of the ozone degradation cycle, the ozone level in the incubator decreases from 400 ppm to less than 1 ppm. In another non-limiting example, a system 10 includes a sterilization unit 16 having a corona discharge ozone generator with sixteen (16) corona plates. In this example, the system 10 includes an environment 12 with an enclosed space within a vehicle. The enclosed space in this example is the rear compartment of an ambulance. The rear compartment has a volume of about 350 ft$^3$ in this example. Other examples include ambulances having rear compartments with a greater volume, such as but not limited to about 375 ft$^3$, about 400 ft$^3$, about 425 ft$^3$, about 450 ft$^3$, about 475 ft$^3$, about 500 ft$^3$, about 525 ft$^3$, about 550 ft$^3$, about 575 ft$^3$, and as much as about 850 ft$^3$. The sterilization unit 16 achieves an ozone level about 15 ppm during the ozone generation cycle. Within 30 minutes of the start of the ozone degradation cycle, the ozone level in the ambulance compartment decreases from about 15 ppm to less than 1 ppm. In still another non-limiting example, a sterilization unit 16 achieves an ozone level of about 30 ppm during the ozone generation cycle. Accordingly, sterilization units 16 described herein can very quickly and safely sterilize ambulances having rear compartments that range in volume from about 350 ft$^3$ to about 850 ft$^3$, as well as degrade ozone in the rear compartment at an accelerated rate in order to quickly return the air in the rear compartment to a safe ozone level.

The sterilization unit 16 features hardware and/or software to collect and/or record information including cleaning time, date, and area for documentation. The sterilization unit 16 can feature on-board WiFi, Bluetooth, and/or RFID systems to record, store, and transmit data.

Implementations of sterilization units 16 described herein are portable and powerful. The sterilization unit 16 can sterilize various environments including research facilities, electronics, hospitals, ambulances, police and military vehicles, ships, tanks, and trains. The sterilization unit 16 provides maximum protection against germs with minimum effort and risk.

Although certain example enclosed spaces are described as "ambulances" or as the rear compartment of an "ambulance," the skilled artisan will understand that the system 10 and sterilization units 16 can be used in any enclosed space, in any confined space that provides medical treatment or care, in any vehicle, and in any emergency and non-emergency vehicle (whether or not the vehicle transports persons or patients). Example vehicles including enclosed spaces that can be sterilized using systems and methods described herein include, but are not limited to, emergency ambulances (providing care to patients with an acute illness or injury, including road-going vans, boats, helicopters, fixed-wing aircraft); patient transport ambulances (transporting patients to and from places of medical treatment for non-urgent care, including vans, buses, and other vehicles); and response units (used to reach an acutely ill patiently quickly and provide on-scene care but lacks the capacity to transport the patient from the scene, including standard cars and fire engines).

Advantageous aspects of the system 10 and the sterilization unit 16 described herein eliminate the need to spend substantial amounts of time and money to plan and deal with the complexity of chemical decontaminations. The sterilization unit 16 eliminates the waste of labor and time associated with decontamination. Further, the sterilization unit 16 eliminates exposure to toxic chemicals and the possibility of chemical residue accumulation.

Example Sterilization Unit

Additional aspects and features of one, non-limiting sterilization unit 16 will now be described with reference to FIGS. 4A-9. It will be understood that although implementations of a sterilization unit 16 will be described with reference to a sterilization unit 100, sterilization units 16 described above with reference to FIGS. 1-3 and the system 10 need not include all features of the sterilization unit 100

Figure 4A:
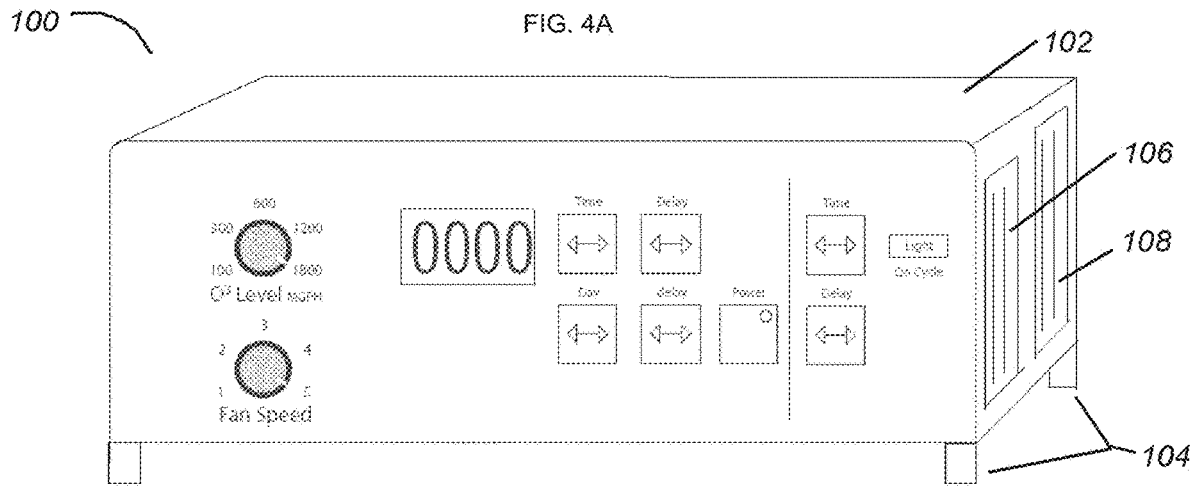
FIG. 4A provides a perspective view of one embodiment of a sterilization unit that can be used in the ozone sterilization system of FIG. 1.

FIG. 4A provides a perspective view of one embodiment of a sterilization unit 100. The sterilization unit 100 can be an ozone generation and degradation unit. In the embodiment of FIG. 4A, the sterilization unit 100 is a semi-mobile unit having a single outer housing 102 and feet 104 and configured for placement on a shelf or floor of an enclosed space. In other embodiments, the sterilization unit 100 is a fully mobile unit having features to facilitate movement of the unit, such as, for example, one or more handles and/or one or more wheels. In other embodiments, the sterilization unit 100 is a semi-permanent or fully permanent fixture, which can be installed within an enclosed space. For example, in some embodiments, the sterilization unit 100 is placed onto a shelf within a piece of laboratory equipment, such as a laminar flow hood, a cell culture chamber, or a refrigerator. In other embodiments, the sterilization unit 100 is configured to be carried or rolled into hospital rooms, hotel rooms, gym locker rooms, and other enclosed spaces. In still other embodiments, the sterilization unit 100 is configured to be installed in an enclosed space such that it is affixed to or within a wall, ceiling, or floor of a room or piece of laboratory equipment.

The sterilization unit 100 of various embodiments is configured to decontaminate and/or sterilize an enclosed space by generating the powerful oxidant, ozone, and releasing the ozone into the enclosed space. In some embodiments, the enclosed space is air-tight, such as, for example, in a cell culture chamber or a laminar flow hood. In other embodiments, the enclosed space is not air-tight. In some such embodiments, the enclosed space is a room or portion of a dwelling having walls, doorways, and/or windows that do not fully seal in gases, such as, for example, in hotel rooms, hospital rooms, medical facilities, gyms, and bathrooms. In some embodiments, the enclosed space may be substantially but not fully enclosed, such as, for example, the space within a gym locker, wherein the locker has holes on its front face. In other embodiments, the enclosed space is an automobile. One having skill in the art will appreciate that the invention is not limited by the location in which it is used, and it is herein contemplated that the sterilization unit 100 may be used in any partially, substantially, and/or fully enclosed space that is in need of sterilization and capable of safely handling brief periods of ozone exposure. As non-limiting examples, the sterilization unit of various embodiments may be used to: disinfect the inner chambers of laboratory and medical equipment, eliminate smoke particulates and odors from rental cars and hotel rooms, and kill germs present in hospital rooms, medical facilities, and gyms.

In various embodiments, the sterilization unit 100 generates ozone during an ozone generation cycle. In such a cycle, air is guided from the enclosed space through one or more air vents (not visible) on a first side of the sterilization unit 100 and into an ozone generation cavity (not visible in FIG. 4A) where oxygen in the air is converted to ozone. The ozonized air is then dispelled out one or more air vents 106 on a second side of the sterilization unit 100 back into the enclosed space. The oxidative and reactive ozone in the air has a sterilizing effect within the enclosed space. An ozone generation cycle may continue for a specific amount of time or until a specific ozone concentration is reached within the enclosed space.

In order to limit potential exposure to ozone, the sterilization unit 100 of various embodiments is also configured to accelerate ozone degradation in the enclosed space.

During ozone degradation, the oxidative and reactive ozone is broken down to the stable and safe compound, oxygen. In various embodiments, the sterilization unit 100 accelerates ozone degradation at least during an ozone degradation cycle once sterilization is complete. In such a cycle, ozonized air is guided from the enclosed space through one or more air vents (not visible) on a first side of the sterilization unit 100 and into an ozone degradation cavity (not visible in FIG. 4A) where the ozone in the air is converted back to a stable oxygen molecule. The de-ozonized air is then dispelled out one or more air vents 108 on a second side of the sterilization unit 100 back into the enclosed space. Through this cycle, ozone is removed from the air, thereby making the air safe for human exposure.

Figure 4B:
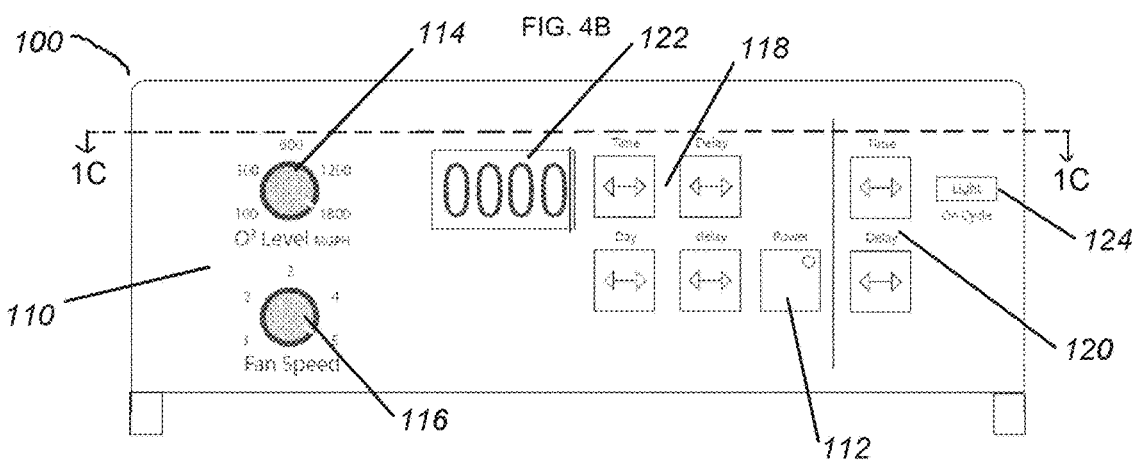
FIG. 4B provides a front view of the sterilization unit of FIG. 4A.

Numerous attributes of these ozone generation and degradation cycles can be controlled by a user through a user interface, such as through the control panel 110 shown in FIG. 4B. In various embodiments, a user can control one or more of the following settings through the user interface 110 of the sterilization unit 100: fan speed, ozone generation intensity, length of ozone generation and/or ozone degradation cycles, and start time of ozone generation and/or ozone degradation cycles. For example, with the control panel 110 of FIG. 4B, a user can power the unit 100 on and off by pressing a power button 112. In the depicted embodiment, a user can turn an ozone level knob 114 to control the intensity of the ozone generator and regulate the rate of ozone production, as measured, for example, in milligrams per hour. A user can also turn a fan speed knob 116 to regulate the speed at which air is pulled from an enclosed space into an ozone generation cavity. A series of buttons 118 also exist for setting the day and time at which an ozone generation cycle is to start. Alternatively, a user can press buttons 118 to program a delayed start. As a non-limiting example, in some environments, a user may turn on the sterilization unit 100 near the end of a work day by pressing the power button 112 and set a 30-minute delay so that ozone production does not begin for 30 minutes, giving all personnel time to leave the enclosed space. The buttons 118 can also be manipulated to set the duration of the ozone generation cycle. In the present embodiment, a series of buttons 120 also exist for controlling the ozone degradation cycle. A user can manipulate the buttons 120, for example, to sets the duration of the ozone degradation cycle. Doing so sets the duration during which air-moving components present in the sterilization unit 100 actively move air through an ozone degradation cavity. A user may also toggle the buttons 120 to set a delayed start. For example, a user can program the sterilization unit 100 to begin blowing air through the ozone degradation cavity one hour (or any other desired length of time) after the ozone generation cycle has begun. Various displays may be present to alert users of the current status of the sterilization unit 100. For example, in FIG. 4B, the power button 112 contains a light, which is illuminated when the sterilization unit 100 is in an "on" state. A display 122 is also present to provide a countdown of the time remaining in an ozone generation cycle. In some embodiments the display 122 or other display (not shown) provides a countdown of the time remaining until an ozone generation cycle is scheduled to begin. An alert light 124 also illuminates when an ozone degradation cycle is in progress.

In various other embodiments, the user interface includes a touchscreen, physical buttons, keys, knobs, and/or any other input elements that are suitable for manipulating the settings of the sterilization unit and are known to one skilled in the art. In addition to receiving inputs from a user, the user interface is also designed to display outputs. The user interface of various embodiments includes one or more lights, visible messages and/or audible alarms to provide users with information about the status of the sterilization unit.

In another embodiment (not shown), a user can use various features of the user interface to input the cubic size of the enclosed space and a peak ozone concentration the user wishes to achieve within the enclosed space. In such an embodiment, the sterilization unit is programmed to calculate the appropriate run time for ozone generation, and optionally, for ozone degradation. In another embodiment (not shown), the sterilization unit is equipped with one or more sensors configured to detect the humidity, pressure, temperature, and/or current ozone level in the enclosed space. Such a sterilization unit is configured to calculate and set the appropriate run time for ozone generation and/or ozone degradation, based in part, on these parameters.

The user interface 110 of FIG. 4B is designed as an integrated control panel disposed on a front face of the sterilization unit 100. In other embodiments, the user interface is positioned on a top face or side face. In still other embodiments, the user interface is positioned on a separately located control panel, a remote control, or other device in wired or wireless communication with the sterilization unit. For example, in some embodiments, the sterilization unit is controllable through a user's cell phone or computer. In such embodiments, commands are sent to the sterilization unit from a remote user interface via radiofrequency, WiFi, Bluetooth, and/or near-field communications. The remote user interface may be positioned outside of the enclosed space while the remainder of the sterilization unit is disposed within the space.

In some embodiments of a sterilization unit, ozone generation and ozone degradation occur within separate cavities within an integrated unit. For example, as shown in the cross-sectional view of the sterilization unit 100 in FIG. 4C, ozone generation occurs within an ozone generation cavity 130 and ozone degradation occurs within an ozone degradation cavity 140. While air flow through the ozone generation cavity 130 and ozone degradation cavity 140 is separated, the two cavities are positioned next to each other and contained within the same outer housing 102. Thus, in some aspects, sterilization units described herein include an outer housing enclosing a first housing and a second housing, the first housing including an ozone generation cavity and the second housing including an ozone degradation cavity.

In other embodiments (not shown), the ozone generation cavity and the ozone degradation cavity are contained in separate, unattached housings. In such embodiments, the ozone generation cavity and the ozone degradation cavity can each be installed or positioned in different locations within the enclosed space. For example, in one aspect, the ozone generation cavity and the ozone degradation cavity are not integrated into an outer housing and are located some distance away from each other at different locations within the enclosed space to be decontaminated. Thus, embodiments of the sterilization unit described herein can include an ozone generation cavity and an ozone degradation cavity that are physically positioned a distance away from each other within the enclosed space, such as but not limited to 1, 2, 3, 4, 6, 8, 10, 12, or more feet away from each other. As a non-limiting example, in one embodiment of the sterilization unit, the ozone generation cavity is installed near the top of an enclosed space while the ozone degradation cavity is installed near the base or bottom of the enclosed space. In another non-limiting example, a first housing including an ozone generation cavity and a second housing including an ozone degradation cavity are not enclosed within the same outer housing. The first housing and the second housing in this example are located a distance away from each other at different locations within the enclosed space.

Figure 4C:
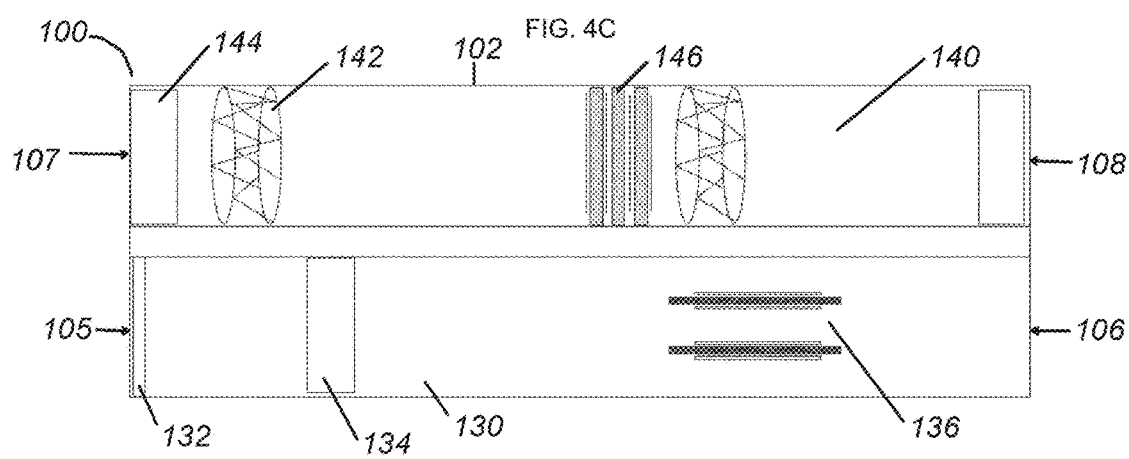
FIG. 4C provides a cross-sectional view of the sterilization unit of FIGS. 4A and 4B, as viewed along the cut-line provided in FIG. 4B.

Continuing with FIG. 4C, the ozone generation cavity 130 is positioned between a first inlet 105 and a first outlet 106. The first inlet 105 and outlet 106 each comprise one or more holes, slots, or other openings in the housing 102, through which air from the enclosed space can enter and exit, respectively, the ozone generation cavity 130. The ozone generation cavity 130 includes, at least, an ozone generator 136 disposed within the ozone generation cavity 130. In the depicted embodiment, an air filter 132 is positioned in the ozone generation cavity 130 between the first inlet 105 and the ozone generator 136. In other embodiments, the air filter 132 is positioned within or on the exterior side of the first inlet 105. The air filter 132 is configured to remove dust, dirt, and other large particulates from the air before the air reaches the ozone generator 136.

The ozone generation cavity 130 of FIG. 4C also includes a first air-moving component 134 disposed within the cavity 130. In some embodiments, a plurality of first air-moving components 134 are present within the cavity 130 and positioned between the first inlet 105 and the ozone generator 136. In other embodiments, a plurality of first air-moving components 134 are positioned in the cavity 130 between the ozone generator 136 and the first outlet 106. Other embodiments have one or more first air-moving components 134 on the inlet side of the ozone generator 136 and one or more first air-moving components 134 on the outlet side of the ozone generator 136. In still other embodiments, the one or more first air-moving components 134 may be positioned within or on the exterior side of the first inlet 105 and/or within or on the exterior side of the first outlet 106. In FIG. 4C, the first air-moving component is a fan. In other embodiments, the first air-moving component is an air blower or any other air-moving element know to one having skill in the art. When the first air-moving component 134 is in operation, it pushes or pulls air from the surrounding enclosed space through the first inlet 105 and the air filter 132, past the ozone generator 136, and out the first outlet 106. That is, in operation, the first air-moving component 134 cycles air between the enclosed space and the ozone generation cavity, helping to dispel ozone into the enclosed space.

As also shown in FIG. 4C, the ozone degradation cavity 140 is positioned between a second inlet 107 and a second outlet 108. The second inlet 107 and a second outlet 108 each comprise one or more holes, slots, or other openings in the housing 102, through which air from the enclosed space can enter and exit, respectively, the ozone degradation cavity 140. The ozone degradation cavity 140 of various embodiments includes, at least, an ozone degrader 146.

The ozone degradation cavity 140 of FIG. 4C also includes two vortex plates 142 and two second air-moving components 144. One having skill in the art will appreciate that in other embodiments, a different number of vortex plates 142 and/or second air-moving components 144 may be present, for example, zero, one, three, or four. Each of the vortex plates 142 and second air-moving components 144 may be positioned: within the ozone degradation cavity 140 between the second inlet 107 and the ozone degrader 146, within the ozone degradation cavity 140 between the ozone degrader 146 and the second outlet 108, in the second inlet 107, in the second outlet 108, or on the exterior side of the second inlet 107 or second outlet 108. In FIG. 4C, the second air-moving components 144 are fans. In other embodiments, air blowers or other air-moving elements are used. In various embodiments, the second air-moving components 144 are configured to push or pull air from the surrounding enclosed space through the second inlet 107, past the ozone degrader 146, and out the second outlet 108, thereby cycling air between the enclosed space and the ozone degradation cavity. The vortex plates 142, when present, are configured to generate at least partially vortical or turbulent airflow. By generating non-laminar airflow, more ozone within the air makes contact with the ozone degrader 146; such an arrangement may accelerate the rate of ozone degradation. In some embodiments, the vortex plates 142 are formed of a plurality of fixed fan fins. In other embodiments, other vortex-inducing designs are used.

In some embodiments, the sterilization unit 100 includes one or more shutters or valves (not shown) positioned within the second inlet 107, in the ozone degradation cavity 140, and/or on the exterior side of the second inlet 107 and/or second outlet 108. The one or more shutters or valves are configured to prevent air from flowing through the ozone degradation cavity 140 when an ozone degradation cycle is not in progress. For example, the one or more shutters or valves remain closed during ozone generation cycles, allowing large concentrations of ozone to build up within the enclosed space. After the ozone generation cycle terminates, the one or more shutters or valves open to initiate the ozone degradation cycle and allow air to cycle past the ozone degrader 146.

In addition to the components described above, various embodiments of the sterilization unit include a rechargeable battery, disposable batteries, and/or cords and a plug for receiving power from an external source. While such batteries, power cords, wiring, and internal electrical connections are not shown in FIG. 4C, it is to be understood and herein contemplated that these can be included and positioned in any suitable manner known to a person skilled in the art.

Figure 5A:
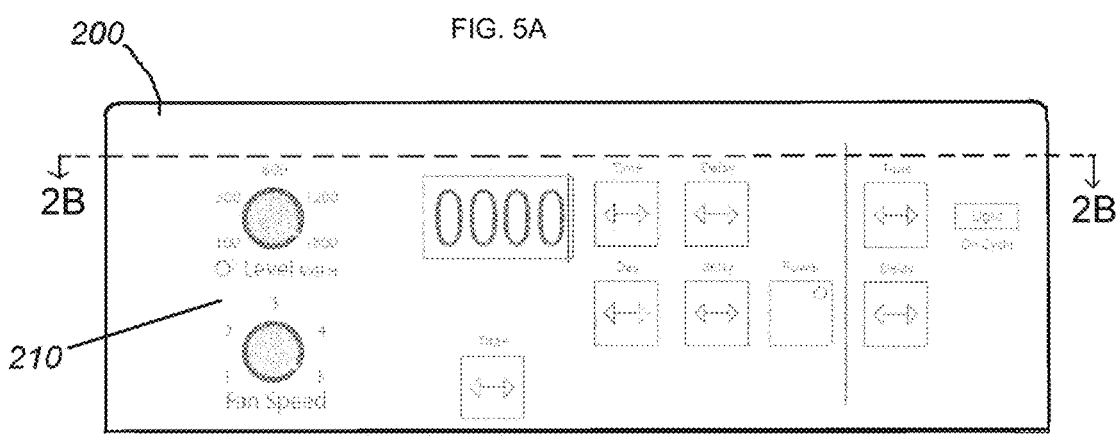
FIG. 5A provides a front view of another embodiment of a sterilization unit.

An additional embodiment of a sterilization unit 200 is provided in FIG. 5A. The sterilization unit 200 can be an ozone generation and degradation unit. In the provided embodiment, a user is able to adjust the buttons and knobs of the control panel 210 in order to set the ozone generation level and the fan speed, and the user may choose to set the values to correspond to particular dimensions and sterilization needs of the enclosed space. The user may also set the duration of the ozone generation cycle, the duration of the ozone degradation cycle, and/or a time delay for the start of the ozone generation and/or degradation cycles. Using such time delay features, a user may, for example, program the unit to begin the ozone generation cycle at the end of the day when no one is using or within the enclosed space. Upon reaching the set ozone level, the unit of various embodiments is programmed to end the ozone generation cycle and begin the ozone degradation cycle, and it may be programmed to terminate the ozone degradation cycle and return the enclosed space to safe ozone levels before anyone returns to the enclosed space the next day.

Figure 5B:
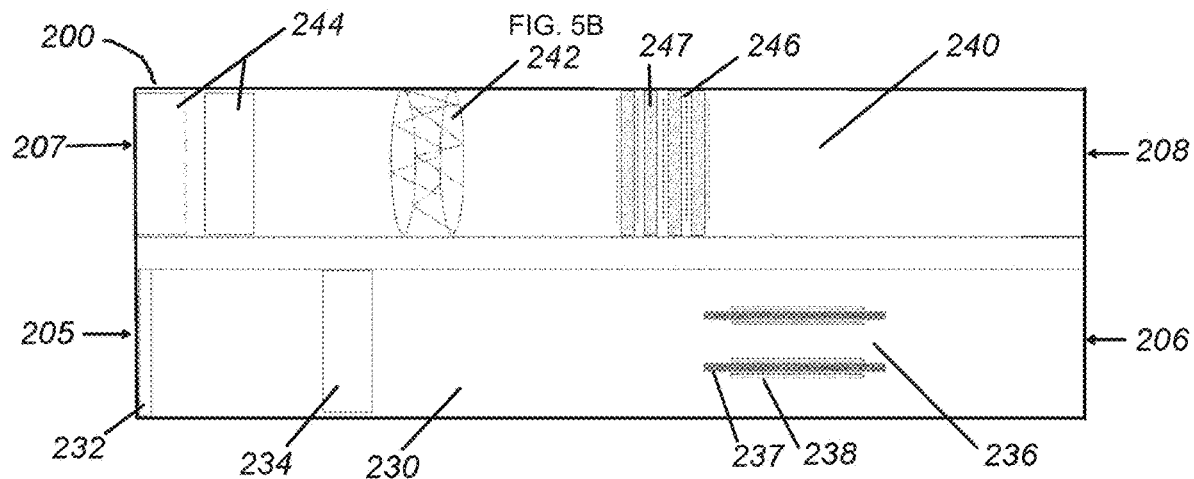
FIG. 5B provides a cross-sectional view of the sterilization unit of FIG. 5A.

As shown in the cross-sectional view of FIG. 5B, the ozone generation cavity 230 of FIG. 5B is positioned between a first inlet 205 and a first outlet 206 and includes an air filter 232, a first air-moving component 234, and an ozone generator 236. In one non-limiting example, the first air-moving component 234 includes a fan. Any ozone generator known to those skilled in the art may be used. In some embodiments, the ozone generator is a corona discharge ozone generator. In other embodiments, an ultraviolet ozone generator or a vacuum-ultraviolet ozone generator is used. In the embodiment depicted in FIG. 5B, the ozone generator 236 includes two ceramic plates 237, with each of the ceramic plates 237 at least partially coated or wrapped with a layer 238 comprising a heavy metal. Particularly, in FIG. 5B, each ceramic plate is partially surrounded by a stainless steel mesh 238 that is coated with a layer of pure silver. In other embodiments, the mesh 238 surrounding each ceramic plate 237 additionally or alternatively includes copper, nickel, cobalt, zinc, iron, gold, or any combination thereof. In such an arrangement, one of the ceramic plates 237 wrapped in a metallic mesh 238 forms an anode and the other ceramic plate 237 forms a cathode. In operation, a high voltage is applied across the anode and cathode arrangement, creating an electric field between the plates 237. As air passes through the electric field between the plates 237, the oxygen molecules present in the air become excited and some dissociate, forming unstable oxygen atoms. The oxygen atoms then react with other oxygen molecules to form ozone.

In some embodiments, the application of a voltage across the ceramic plates 237 also excites the heavy metal or metals that are at least surrounding or coating the plates 237. Such excitation may cause heavy metal ions to be produced and released into the enclosed space with the ozonized air. In the arrangement shown in FIG. 5B, the application of a high voltage to the ceramic plates 237 produces both ozone and silver ions. Silver ions have preliminarily been shown to have an antimicrobial effect, helping to augment the sterilizing effect of the ozone. With such an arrangement, even hard to kill biologic materials, such as T1 bacteriophages have been killed in experiments, as described in more detail below. The ozone generator of some embodiments is configured to produce a gas that includes both ozonized air and heavy metal ions. In some such embodiments, the ozone generator is configured to produce a gas that includes ozonized air and silver ions.

Continuing with FIG. 5B, the ozone degradation cavity 240 is positioned between a second inlet 207 and a second outlet 208, and includes one or more second air-moving components 244, a vortex plate 242, and an ozone degrader 246. In one non-limiting example, the one or more second air-moving components 244 include one or more fans. In one embodiment, the one or more second air-moving components 244 include two fans. Any ozone degrader capable of accelerating the breakdown of ozone to oxygen, which is known to those skilled in the art may be used. The ozone degrader 246 of some embodiments is selected from the group consisting of: an ozone oxidation catalyst, a catalytic filter, a filter and any combination thereof. For example, in some embodiments, the ozone degrader 246 is formed of a metal alloy catalyst, such as, for example, a manganese oxide, platinum-iridium, or platinum-palladium catalyst. In some embodiments, the ozone degrader is formed, at least in part, of activated carbon. In FIG. 5B, the ozone degrader 246 is formed of activated carbon-based filters 247 sandwiched closely together. The filters 247 are formed of mesh copper with activated carbon bound to the copper. In some embodiments, the activated carbon may be bound to a different metallic mesh. In other embodiments, a layer of activated carbon particles may be compressed between layers of metallic or non-metallic mesh or nonwoven fabric material. In FIG. 5B, four activated carbon-based filters are present. In other embodiments, one, two, three, or more activated carbon-based filters are used to convert ozone to oxygen.

Figure 6:
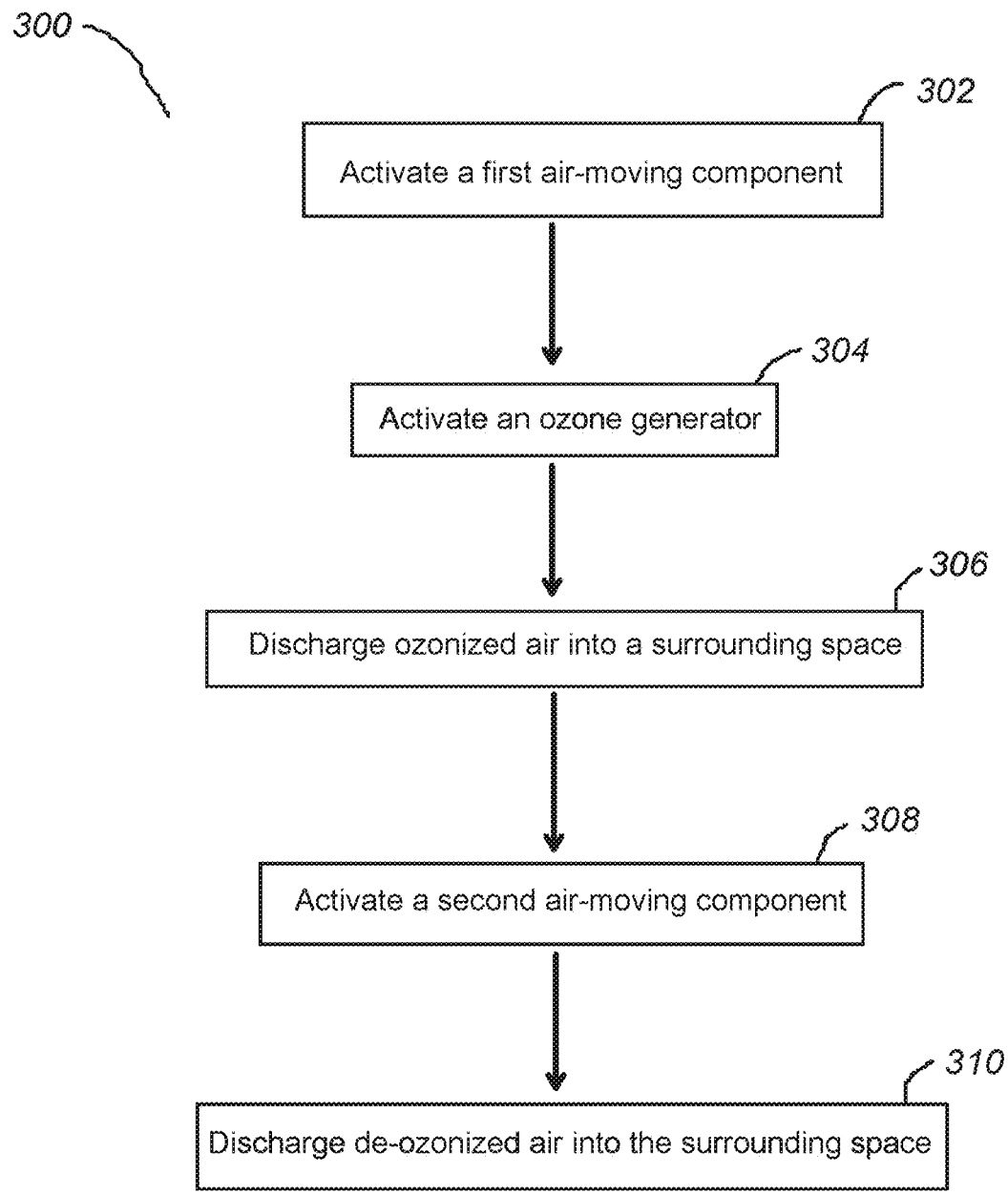
FIG. 6 provides a flow chart of one embodiment of a method of decontaminating and/or sterilizing an enclosed space.

FIG. 6 provides a flow chart 300 depicting one embodiment of a method of sterilizing and/or decontaminating an enclosed space using a sterilization unit, such as, for example, sterilization unit 100 or 200 positioned within the enclosed space. When describing the components used to perform the method, reference will be made to FIGS. 5A and 5B. Throughout the described embodiment, information and signals may be represented by voltages, currents, electromagnetic waves, magnetic fields or particles, optical fields or particles, or any combination thereof.

As shown at block 302, the sterilization unit 200 supplies electrical signals to a first air-moving component 234 positioned in or near the ozone generation cavity 230 in order to activate the first air-moving component 234. Activating the first air-moving component 234 moves air containing oxygen from the enclosed space into the ozone generation cavity 230 and into contact with an ozone generator 236. At block 304, the sterilization unit 200 supplies electrical signals to the ozone generator 236, which activates the ozone generator 236 and causes at least some of the oxygen in the air to convert to ozone. At block 306, ozonized air is discharged from the ozone generation cavity 230 into the enclosed space. The ozonized air exits the ozone generation cavity 230 through a first outlet 206. This discharge of ozonized air occurs in response to the continued operation of the first air-moving component 234. In some embodiments, this cycle of generating ozonized air and discharging it into the enclosed space is repeated until the air in the enclosed space reaches a measurable ozone concentration, such as, for example, 0.1 ppm. In other embodiments, the cycle continues for a set period of time or until the air in the enclosed space reaches an ozone concentration sufficient for sterilization, such as, for example, at least 60 ppm. In some embodiments, the cycle continues until the air in the enclosed space reaches an ozone concentration of at least 140 ppm. In some embodiments, the cycle continues until the air in the enclosed space reaches an ozone concentration of between about 140 and about 150 ppm. In some embodiments, the cycle continues until the air in the enclosed space reaches an ozone concentration of at least 325 ppm.

At block 308, the sterilization unit 200 supplies electrical signals to a second air-moving component 244 positioned in or near the ozone degradation cavity, thereby activating the second air-moving component 244. Activating the second air-moving component 244 moves ozonized air from the enclosed space into the ozone degradation cavity 240 and into contact with the ozone degrader 246. In various embodiments, the ozone degrader 246 is a filter or other non-electrical component, thus, the ozone degrader 246 does not require activation. Making contact with the ozone degrader 246 is sufficient to cause at least some of the ozone to convert to oxygen molecules, thereby reducing the ozone content in the air. At block 310, de-ozonized air is discharged into the enclosed space. The de-ozonized air exits the ozone degradation cavity 240 through a second outlet 208. This discharge of de-ozonized air occurs in response to the continued operation of the second air-moving component 244. In some embodiments, this cycle of discharging de-ozonized air into the enclosed space is repeated until the air in the enclosed space reaches a safe ozone concentration, such as, for example, a concentration of less than 0.1 ppm. In other embodiments, the cycle continues for a set period of time.

In some embodiments, information about when to initiate each of the blocks described above may be received from a user supplying inputs through a user interface 210. The steps of a method and functions described above, in connection with the embodiments disclosed herein, may be embodied directly in hardware, in a software module executed by a processor, or in a combination of the two. If implemented in hardware, the methods may be implemented or performed with, or controlled by, any suitable means capable of performing the operations, including a general purpose processor, a Digital Signal Processor (DSP), an Application Specific Integrated Circuit (ASIC), a Field Programmable Gate Array (FPGA), or other programmable logic device, discrete gate or transistor logic, discrete hardware components, or any combination thereof designed to perform the functions described herein. A general purpose processor may be a microprocessor, but in the alternative, the processor may be any processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

If any of the steps of a method or functions described above are implemented in software, the functions may be stored on or transmitted over as one or more instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. In some embodiments, a storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

A similar method is performed by the embodiment of the sterilization unit 400 of FIGS. 7A-7D. The sterilization unit 400 can be an ozone generation and degradation unit. In the present embodiment, the user interface/control panel is separated from, and in wireless communication with, the remainder of the unit.

In the embodiment of FIGS. 7A-7D, the first inlet 405 into the ozone generation cavity 430 is positioned on the top face of the unit 400. The first outlet 406 to the ozone generation cavity 430 is positioned on the bottom face of the unit 400. Conversely, the second inlet 407 into the ozone degradation cavity 440 is positioned on the bottom face of the unit 400 and the second outlet 408 to the ozone degradation cavity 440 is positioned on the top face of the sterilization unit 400. In the depicted embodiment, the unit 400 is provided with feet 404 to elevate the sterilization unit 400 and provide for airflow between the bottom face of the unit and the enclosed space.

Advantageously, such a configuration may provide for more efficient ozone generation and degradation. Ozone is heavier than oxygen and has been found to largely settle to the bottom of an enclosed space. Accordingly, during the ozone generation cycle, oxygen-rich air, which largely rests above the ozone-rich air, can readily be pulled from above through the first inlet 405 on the top face of the sterilization unit 400. The ozonized air can then be dispelled downward through the first outlet 406 on the bottom face of the sterilization unit. The ozonized air can then settle near the bottom of the enclosed space. In this manner, oxygen-rich air, still in need of being ozonized, may be pulled into the ozone generation cavity 430 at a greater rate than the air that has already been ozonized, thus increasing the efficiency of the ozonizing process. Similarly, during the ozone degradation cycle, ozonized air, present in greater concentrations near the bottom of the enclosed space than the top of the enclosed space, can be pulled into the ozone degradation cavity 440 with greater efficiency by pulling the ozonized air through a second inlet 407 positioned on the bottom face of the sterilization unit 400 and expelling the de-ozonized air upward through a second outlet 408 positioned on the top face of the sterilization unit 400.

Figure 7A:
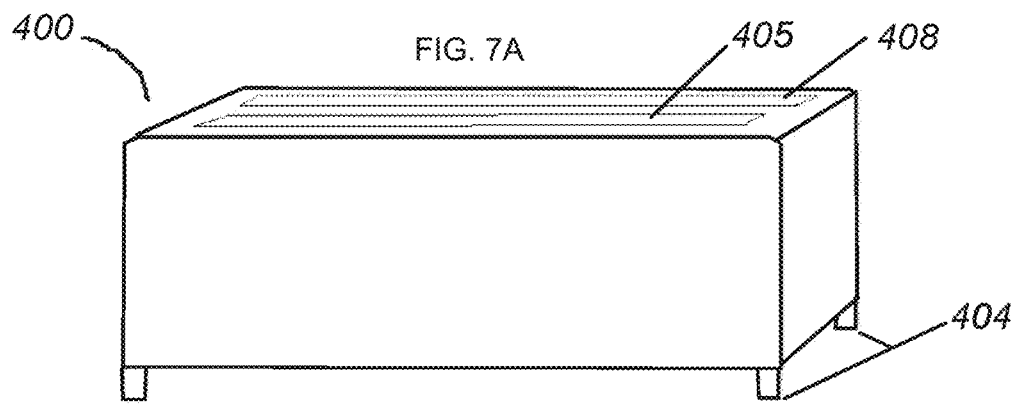
FIG. 7A provides a perspective view of an embodiment of a sterilization unit.
Figure 7B:
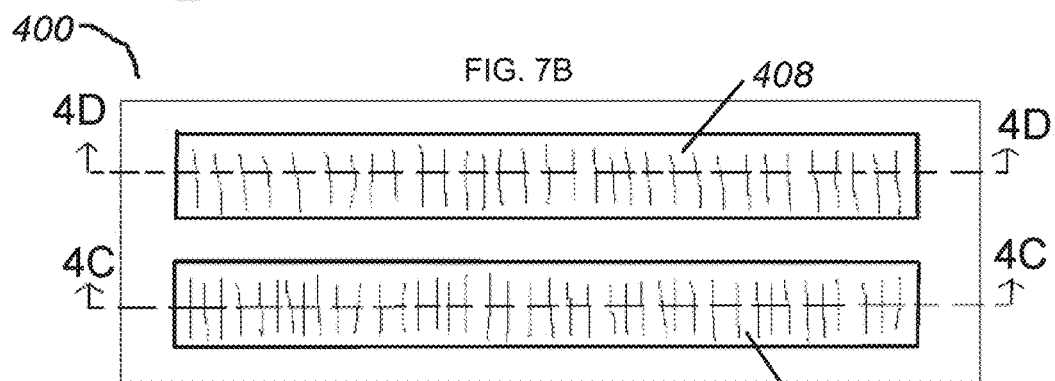
FIG. 7B provides a top view of the sterilization unit of FIG. 7A.
Figure 7C:
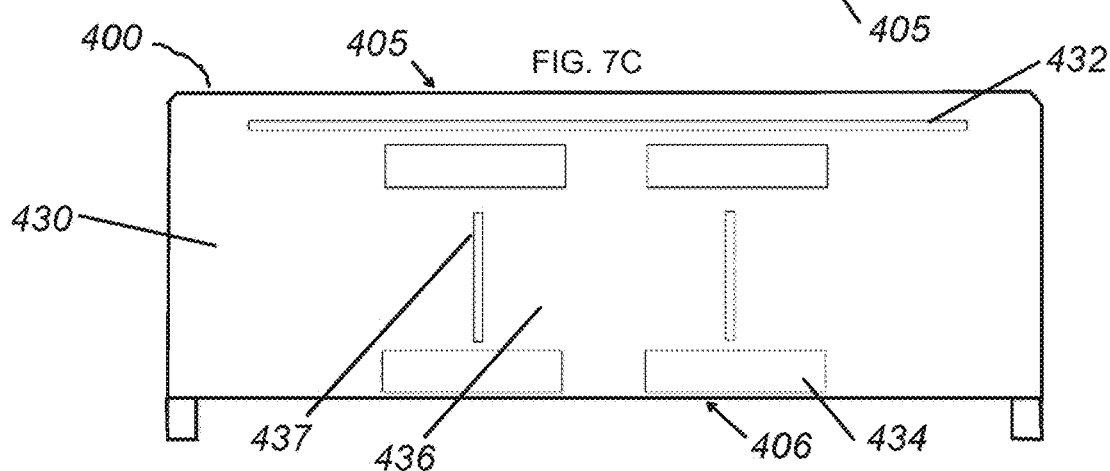
FIG. 7C provides a cross-sectional view of the sterilization unit of FIGS. 7A and 7B, as viewed along the corresponding cut-line of FIG. 7B.

As shown in the cross-section of the ozone generation cavity 430 in FIG. 7C, during the ozone generation cycle, a plurality of fans 434 operate to pull air through the first inlet 405, through an air filter 432, between the plates 437 of the ozone generator 436, and out the first outlet 406. During this time, the ozone generator 436 is also activated and a high voltage is present between the plates 437 of the ozone generator 436, so that at least some of the oxygen in the air passing between the plates 437 is converted to ozone. This cycle of ozone generation can be programmed to continue for a specified time or until a specified concentration of ozone is generated.

Figure 7D:
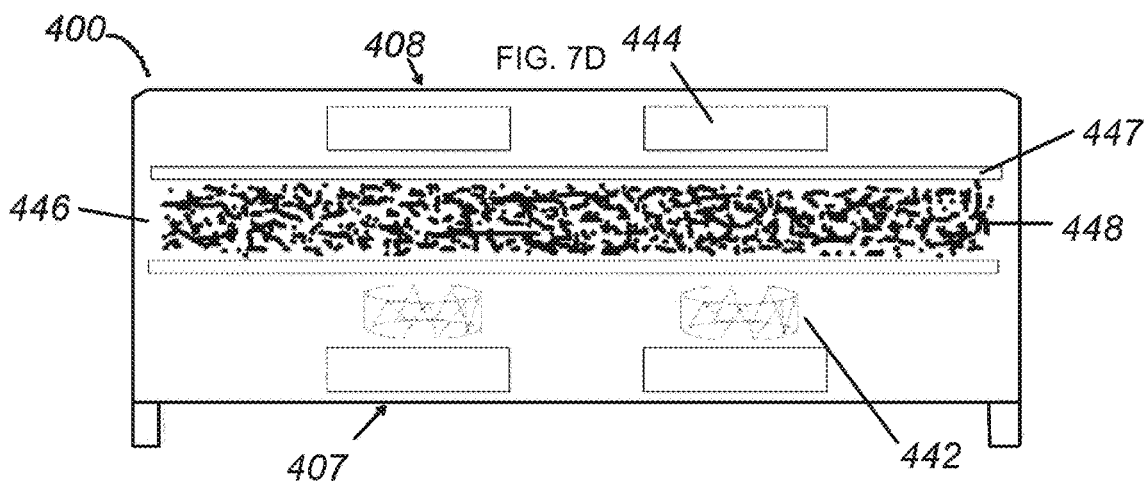
FIG. 7D provides an additional cross-sectional view of the sterilization unit of FIGS. 7A and 7B, as viewed along the corresponding cut-line of FIG. 7B.

As shown in the cross-section of the ozone degradation cavity in FIG. 7D, during the ozone degradation cycle, a plurality of fans 444 operate to pull air through: the second inlet 407, one or more vortex plates 442, and the ozone degrader 446, before being expelled out the second outlet 408. At least some of the ozonized air is de-ozonized as it passes through the ozone degrader 446. In FIG. 7D, the ozone degrader 446 includes a layer of activated carbon particles 448 compressed between two layers of copper mesh 447. In some embodiments, the particles are shaped like pellets. In other embodiments, the particles are shaped like granules, discs, chunks, or any other suitable shape known to those skilled in the art.

FIG. 8 is an exemplary report related to a sterilization unit, such as sterilization unit 16 or sterilization unit 100, 200, 300. As described herein, the unit can record one or more parameters, including parameters of one or more sterilization events performed by the unit. The sterilization event can include, for example, an ozone generation cycle and an ozone degradation cycle performed by the unit after it is placed inside an enclosed space. The parameter can include the date when the unit is turned on or connected to power. The parameter can include the date when the unit is turned off or disconnected from power. The parameter can include the time when the unit is turned on or connected to power. The parameter can include the time when the unit is turned off or disconnected from power. The unit can be turned on or off by using the user interface. The unit can be turned on or off by using a device in wireless communication with the unit, such as a remote control or a mobile app. The unit can be connected or disconnected from power by unplugging the device from a power source. The unit can be connected or disconnected from power by connecting or disconnecting the battery within the unit from the CPU.

The parameter can include the actual run time of the ozone generation cycle. The parameter can include the programmed run time of the ozone generation cycle. The parameter can include the start time of the ozone generation cycle. The parameter can include the end time of the ozone generation cycle. The parameter can include the actual run time of the ozone degradation cycle. The parameter can include the programmed run time of the ozone degradation cycle. The parameter can include the start time of the ozone degradation cycle. The parameter can include the end time of the ozone degradation cycle.

The parameter can include the selected run time by a user. As described herein, the user can select the run time of the ozone generation cycle. The run time of the ozone generation cycle can be 10 minutes, 20 minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, etc. As described herein, the user can select the run time of the ozone degradation cycle. The run time of the ozone degradation cycle can be 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, etc. The programmed run time of the ozone generation cycle can be greater than 1 minute. The programmed run time of the ozone generation cycle can be less than 100 hours. The programmed run time of the ozone generation cycle can be between 1 minute and 100 hours. The programmed run time of the ozone degradation cycle can be greater than 1 minute. The programmed run time of the ozone degradation cycle can be less than 100 hours. The programmed run time of the ozone degradation cycle can be between 1 minute and 100 hours. The run time of the ozone generation cycle and the run time of the ozone degradation cycle can be independently programmed.

The length of the ozone degradation cycle can be related to the length of the ozone generation cycle to ensure that a sufficient amount of ozone that was generated during selected the ozone generation cycle is degraded. In some cases, the user selects the length of the ozone degradation cycle based on the selected length of the ozone generation cycle. In some cases, the unit automatically determines a minimum allowable ozone degradation cycle based on the length of the ozone generation cycle selected by the user. The length of the ozone degradation cycle may be a minimum length of time independent of the selected length of the ozone generation cycle. The length of the ozone degradation cycle may be a length of time previously determined to ensure a safe level of ozone is achieved in the enclosed space prior to the end of the ozone degradation cycle.

The selected run time of the ozone generation cycle and the selected run time of the ozone degradation cycle can be associated with a program. The unit may include a plurality of programs for selection by the user based on, for example, the features of the enclosed space and sterilization needs of the user. The parameter can include the program selected by the user. The program can include a run time of 90 minutes for the ozone generation cycle and a run time of 30 minutes for the ozone degradation cycle. The program can include a run time of 60 minutes for the ozone generation cycle and a run time of 20 minutes for the ozone degradation cycle. The ozone degradation cycle can be greater than 5 minutes. In experiments related to embodiments of units described herein, greater than 90% of the ozone is degraded and removed from the enclosed space within the first 5 minutes of the ozone degradation cycle. In experiments related to embodiments of units described herein, approximately 98% of the ozone is degraded and removed from the enclosed space within the first 5 minutes of the ozone degradation cycle.

The parameter can include an ozone concentration within the enclosed space during a sterilization event as measured by an ozone sensor located within the sterilization unit. The parameter can include the ozone concentration before the ozone generation cycle. The parameter can include the ozone concentration after the ozone generation cycle is complete. The parameter can include the peak ozone concentration after the unit is turned on or connected to power to perform a sterilization event. The parameter can include the peak ozone concentration after the ozone generation cycle is completed. The parameter can include the ozone concentration before the ozone degradation cycle starts. The parameter can include the ozone concentration after the ozone degradation cycle is complete. The ozone concentration measurement may be occur immediately after, 1 minute after, 2 minutes after, 5 minutes, or some other length of time after the ozone degradation cycle is complete. In one example, the sensor transmits one or more signals indicative of ozone concentration to the CPU of the unit, which records the signals. In another example, the sensor wirelessly transmits one or more signals indicative of ozone concentration to a device external to the unit, such as a remote control or a mobile app of a communications device.

The parameter can include an indication that the peak ozone concentration that was achieved during a sterilization event is greater than a threshold value. The parameter can include an indication that the measured peak ozone concentration is greater than a pre-determined peak ozone concentration required to sterilize an enclosed space having particular features (such as total volume or square footage). The user may input information on the features of the enclosed space into the unit using the user interface, the remote control, or the mobile app, and the unit may automatically calculate the required peak ozone concentration. The parameter can include an indication that a peak ozone concentration of 60 ppm was achieved during a sterilization event performed by the unit. The parameter can include an indication that the peak ozone concentration reached 70 ppm. The parameter can include an indication that the peak ozone concentration reached 80 ppm. The parameter can include an indication that the peak ozone concentration reached 90 ppm. The parameter can include an indication that the peak ozone concentration reached 100 ppm. The parameter can include a word or letter (e.g., pass, fail, P indicating pass, F indicating fail, yes, no, Y indicating yes, N indicating no) indicating whether a pre-determined peak ozone concentration was achieved during the sterilization event. The parameter can include the actual peak ozone concentration achieved during the sterilization event as measured by a sensor in the unit.

The parameter can include an indication that the ozone concentration after completion of the ozone degradation cycle is less than a threshold value. The threshold value may be previously determined based on particular features of the enclosed space being sterilized (such as total volume or square footage). The user may input the features into the unit using the user interface, the remote control, or the mobile app, and the unit may automatically calculate the threshold value. The parameter can include an indication that the ozone concentration after the ozone degradation cycle is less than a pre-determined safe ozone concentration. The parameter can include an indication that the ozone concentration after the ozone degradation cycle is complete is less than 0.1 ppm. The parameter can include an indication that the ozone concentration after the ozone degradation cycle is complete is less than 0.2 ppm. The parameter can include an indication that the ozone concentration after the ozone degradation cycle is less than 0.3 ppm. The parameter can include a word or letter (e.g., pass, fail, P indicating pass, F indicating fail, yes, no, Y indicating yes, N indicating no) indicating whether the enclosed safe has returned to a safe ozone concentration after completion of a sterilization event. The parameter can include the actual ozone concentration after the ozone degradation cycle is complete as measured by a sensor in the unit.

The parameter can include the amount of time the unit is turned on or connected to power during a sterilization event, or an aggregate amount of time the unit is turned on or connected to power over a plurality of sterilization events. The unit can include a counter. The counter can track the total number of hours that the unit has been turned on or connected to power since a reference event. The reference event can be, for example, the first time the unit was turned on, a regular maintenance event, or a repair event. In some cases, the counter is reset based on an established periodicity. For example, a user may reset the counter to 0 hours at the beginning of each calendar year. In some embodiments, the counter can be reset to 0 hours after the reference event. The counter can be reset after maintenance or repair. In other embodiments, the counter cannot be reset. Rather, the counter continuously tracks the usable life of the unit.

The parameter can include identification of a tracker. In one non-limiting embodiment, the tracker includes a Radio-frequency identification (RFID) tag. In some embodiments, the RFID tag can be embedded or otherwise located within the environment. The RFID tag can store information such as identifying information for the object to which the RFID tag is attached. In another non-limiting embodiment, the tracker includes an iBeacon®. iBeacon® is an Apple® technology standard which allows mobile apps running on either iOS® or Android® devices to receive data signals from beacons in the real world and, in some case, react to data transmitted in the beacons. iBeacon® allows mobile apps to understand their position in a local environments. The underlying technology of iBeacon® includes Bluetooth Low Energy®. Bluetooth Low Energy® is a wireless network technology that allows for the transmission of data signals over short distances. Bluetooth Low Energy® is designed for low energy consumption, while maintaining the communication range associated with Bluetooth® technology. Bluetooth Low Energy® can be used for periodic transfer of one or more parameters from the unit to a device external to the unit. Bluetooth® can be used for more complex applications, for instance continuous transfer of parameters requiring consistent or constant communication, with more data transmission.

The parameter can include information received and stored in the unit following transmission of data signals from the tracker to the unit. The parameter can include the name of the tracker. The parameter can include the serial number of the tracker. The parameter can include the location of the tracker. The parameter can include an identification of the environment provided by the tracker or extrapolated by the unit based on information provided by the tracker. The environment can be any enclosed space. Examples of environments include ambulances, mobile hospitals, life flight helicopters, urgent and non-urgent vehicles for medical transport, hospital rooms, airplanes, gyms, hotel rooms, rental cars, and laboratory and medical equipment. Each tracker can be associated with a single enclosed space, such as a single ambulance. In some embodiments, a single tracker is associated with each of a plurality of enclosed spaces, such as ambulances, to be sterilized by one or more units. The plurality of ambulances may be physically located near each other. The parameter can include an identification of the tracker that is the shortest physical distance to the unit. Information on the tracker that is physically closest to the unit can be used to identify the particular enclosed space of the plurality of enclosed spaces in which the unit has been placed.

As described herein, the unit can be placed inside a vehicle of a plurality of vehicles. In some cases, the unit is sequentially placed inside each of the plurality of vehicles to sterilize the vehicles. The parameter can include the VIN number of the vehicle in which the unit has been placed, license plate of the vehicle, company that owns, services, and/or uses the vehicle, and/or the make or model of the vehicle. The parameter can include company specific information regarding the environment. The parameter can include a company-assigned number to the vehicle, the shifts associated with the vehicle, and the drivers associated with the vehicle. The parameter can include the volume of the enclosed space of the environment.

The unit can transmit one or more parameters to a database associated with a remote computing resource. The unit can transmit one or more parameters to a database associated with a mobile phone. The unit can transmit one or more parameters to a database associated with the mobile phone with the mobile app 700, described herein. The unit can transmit one or more parameters to a database associated with a tablet, laptop, or other computer. The unit can transmit one or more parameters to a database associated with a database stored on a mobile device. In some embodiments, the user can check one or more parameters in real time using a mobile app. For instance, the user can check the current ozone concentration or indicator during the sterilization event. For instance, the user can check, in real time, the ozone concentration or indicator during and after the ozone generation cycle. In some embodiments, the database is located on the cloud. In some embodiments, the parameters are transmitted wirelessly to the cloud. The unit can transmit one or more parameters per sterilization event during the sterilization event. The unit can transmit one or more parameters during ozone generation cycle. The unit can transmit one or more parameters per ozone degradation cycle. The unit can transmit one or more parameters once the ozone degradation cycle is complete. The unit can transmit one or more parameters once two or more ozone degradation cycles are complete. The unit can transmit one or more parameters once the unit has an established communication path to receive or send a wireless signal. The unit can transmit one or more parameters once a period of time has passed. For example, the unit can transmit one or more parameters daily, weekly, monthly, quarterly, or yearly. The unit can store one or more parameters until the unit can transmit one or more parameters to a database. Accordingly, the unit can transmit parameters to a device external to the unit during sterilization events, and the unit can store and aggregate parameters associated with a plurality of sterilization events performed by the unit and transmit the aggregated data to a device external to the unit.

In one non-limiting example of systems and methods described herein, a system includes a plurality of sterilization units that are deployable to sterilize a plurality of enclosed spaces, such as but not limited to a fleet of ambulances, that are controlled, operated, or owned by a single entity or facility. Each ambulance is equipped with one beacon, such as but not limited to a Bluetooth Low Energy® beacon. A user positions one sterilization unit into a first ambulance in the fleet of ambulances. The user turns the sterilization unit on. The unit automatically searches for signals transmitted by nearby beacon, such as but not limited to a Bluetooth Low Energy® beacon. The unit may receive signals from a plurality of nearby beacons located within a certain range of the unit, including a signal from the beacon installed in the first ambulance. The unit automatically selects the signal that is associated with the beacon that is physically closest to the unit, in this case the beacon associated with the first ambulance in which the unit has been positioned. The unit records a beacon identification number associated with the selected signal. The user programs the unit to perform a sterilization event. The unit records one or more parameters associated with the sterilization event as described herein. The unit transmits the one or more recorded parameters wirelessly to a remote computing resource, such as the cloud. The cloud can consolidate and organize data in reports transmitted by each unit in the plurality of sterilization units. The entity or facility that operates the fleet of ambulances can advantageously receive and analyze a report that consolidates data transmitted by sterilization units during a plurality of sterilization events occurring in the fleet of ambulances.

The system can generate a report from the one or more parameters. FIG. 8 is a sample report. The report can be generated for a customer. The report can include identification of the customer. The identification of the customer can include a customer number (see line 1). The identification of the customer can include a customer location (see line 2). The system can identify the unit owned by the customer (see line 3). For the sample report, the report is for a sterilization unit that has been assigned unit number 100016 in a system of units.

The report can be generated for a period of time (see line 4). The period of time can be daily, monthly, weekly, quarterly, yearly, etc. The report can be generated for one or more trackers. The system can identify one or more trackers associated with the customer.

The report can be generated for one or more trackers associated with the customer. The report can include identification of the one or more trackers. The report can include an identifier such as a name which identifies the tracker (see line 5). The report can include an identifier such as a serial number which identifies the tracker (see line 6). The report shown in FIG. 8 aggregates parameters for Unit No. 100016 that established wireless communications with three trackers when the unit was moved to and performed sterilization events within three different enclosed spaces, each space associated with one of the three trackers.

The report can be generated for one or more cycles associated with a tracker. The report can include an entry which corresponds to a cycle (see line 7). The report can include one or more entries which correspond to one or more cycles (see lines 7-11). Each cycle can include an ozone generation cycle and an ozone degradation cycle. Each cycle can occur in the environment in which the tracker, identified in lines 5-6, is placed. Each cycle can occur with the unit owned by the customer, identified in line 3.

The report can include one or more parameters of the cycle (see line 7). The report can include the date of the cycle (see line 7). The report can include the start time of the cycle (see line 7). The report can include the actual run time of the ozone generation cycle (see line 7). The report can include an indication that the peak ozone concentration is greater than a threshold value (e.g., PASS, see line 7). The report can include the actual run time of the ozone degradation cycle (see line 7). The report can include the actual ozone concentration after the ozone degradation cycle (see line 7). The report can include a counter, or other indication of the aggregate time the unit has been turned on or connected to power since a reference event (e.g. 166 hours, see line 7).

The report can include one or more parameters of a different cycle (see lines 8-11). The report can display differences between one or more parameters associated with different sterilization events, each event including an ozone generation cycle and an ozone degradation cycle. The cycles can occur on different dates. The cycles can occur at different times. The actual run time of the ozone generation cycle can be different for different cycles (see lines 7-9). The actual run time of the ozone generation cycle can be different based on a different program selected by the user (see line 8). The actual run time of the ozone generation cycle can be different if the system is disconnected from power or is turned off (see line 9). The indication of peak ozone concentration can be different for different cycles (see line 7 and 9).

The actual run time of the ozone degradation cycle can be different for different cycles (see lines 7 and 10). The actual run time of the ozone degradation cycle can be different based on a different program selected by the user (see line 10). The actual run time of the ozone degradation cycle can be different if the system is disconnected from power or is turned off (see line 10).

The actual ozone concentration achieved in the enclosed space as measured by a sensor after the ozone degradation cycle is complete can be different based on different cycles (see lines 7-8). The ozone concentration can vary based on environmental factors including heat, humidity, and sunlight. The counter can increase with each cycle (see lines 7-11). The counter can consecutively increase.

The report can be generated for one or more cycles associated with a second tracker. The second tracker can be associated with a different environment, such as a different ambulance. The cycles can occur on during the same period of time (see line 4, 12). The report can include an identifier such as a name which identifies the tracker (see line 13). The report can include an identifier such as a serial number which identifies the tracker (see line 14). The report can include an entry which corresponds to cycles (see line 15-19).

The report can be used by the customer for a variety of uses. The counter can indicate when maintenance is required (e.g., after 100 unit hours, after 200 unit hours, after 300 unit hours, etc.). The cycles can indicate the frequency of sterilization of an environment using a sterilization unit of a plurality of sterilization units. The cycles can indicate whether an environment was skipped on a certain day. The cycles can indicate that an environment was sterilized more often than another environment. The report can indicate how often a unit is used. The report can indicate where a unit is used by identification of the tracker that was physically closest to the unit when a sterilization event was performed. The report can indicate when a unit is used by identification of the date and time. While FIG. 8 shows one example of a report, other reports are contemplated. As one example, the report can include different parameters. As another example, the report can include visual indications such as a line graph for the ozone concentration. As another example, the report can include a different layout. As another example, the report can be prepared for each tracker instead of each unit. As another example, the report can be prepared for each environment instead of each unit.

Figure 9:
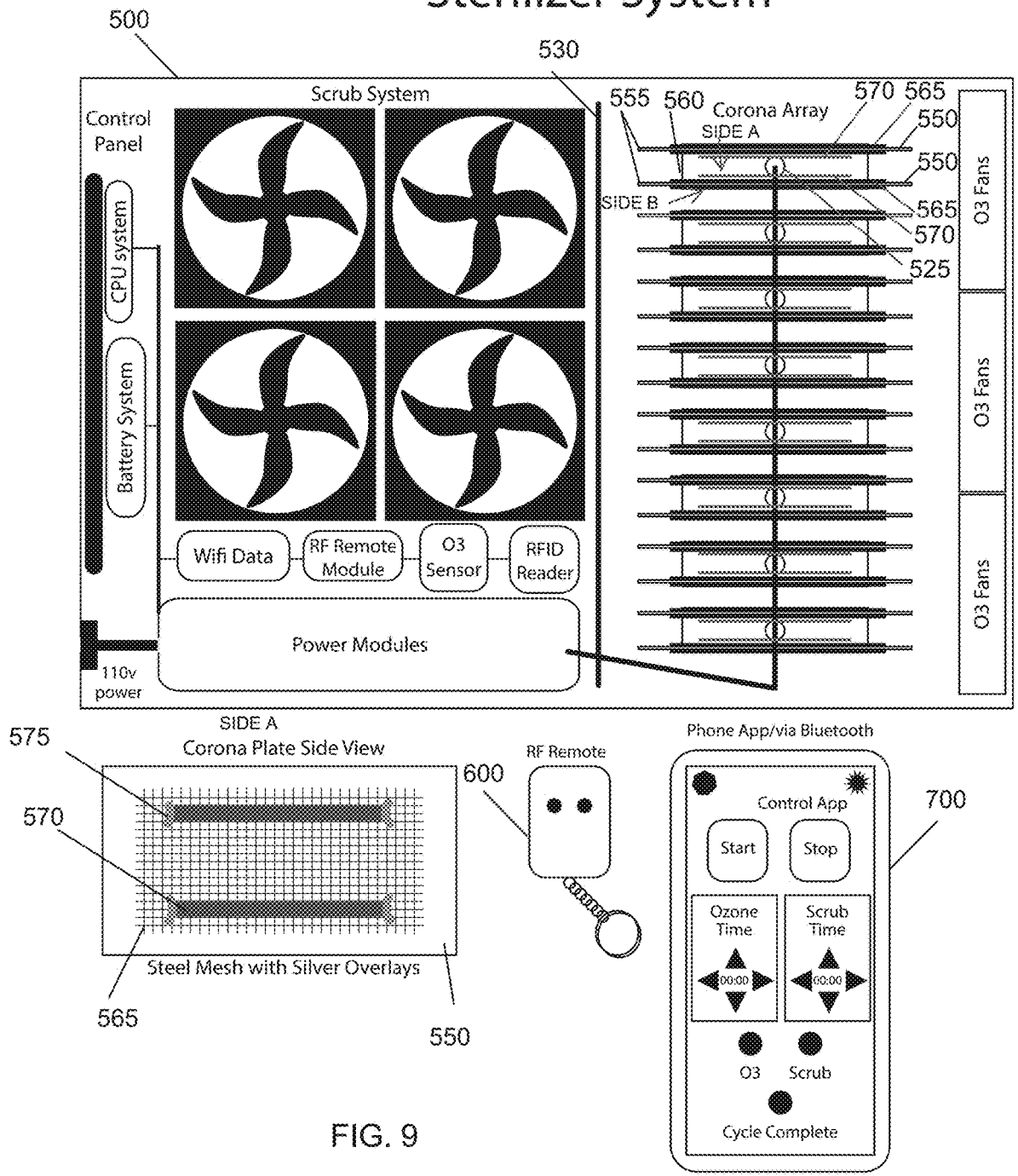
FIG. 9 provides a schematic view of another embodiment of a sterilization unit.

FIG. 9 is an example of a system according to another embodiment. The system can include a sterilization unit 500. The sterilization unit 500 can include any of the features described herein. The sterilization unit 500 can include a control panel. The control panel can accept inputs from the user via a user interface. The control panel can include a central processing unit (CPU) system. The CPU system can include hardware that executes a program. The CPU system can include data storage devices or memory to store programs or information. The CPU system can control the operation and performance of a sterilization event, including for instance an ozone generation cycle and an ozone degradation cycle. The CPU system can receive signals indicative of parameters of one or more cycles. The CPU system can store parameters of one or more cycles. The CPU system can transmit signals, in a wired or wireless configuration, indicative of parameters of one or more cycles of one or more sterilization events.

The control panel can include a battery system. The battery system can supply power to the CPU system in case of power failure. The battery system can supply power to the CPU system in case of power interruption. The battery system can supply power to the CPU system in case a power module is disconnected from a power supply. The battery system can prevent a hard shut down of the CPU system.

The power module can be connected to 110v power, such as through an outlet. The power module can supply power to the CPU system. The power module can supply power to the battery system. The power module can supply power to one or more modules. For example, the power module can supply power to a WiFi data module, an RF remote module, an ozone sensor module, and an RFID reader module. The power module can supply power to a corona array. The power module can supply power to a plurality of ozone fans. The power module can supply power to any component within the sterilization unit 500 or of the system.

The sterilization unit 500 can include one or more modules for communication of data to a device external to the sterilization unit 500. The WiFi data module can send and receive signals on a WiFi network. The WiFi data module can send one or more parameters of a sterilization event to a remote database. The WiFi data module can send one or more parameters of a sterilization event to the cloud.

The RF remote module can send and receive signals to a remote 600. The remote 600 can include one or more buttons to control functions of the sterilization unit 500. In some cases, the remote 600 transmits signals via radio frequency (RF). In some cases, the remote 600 transmits information to the RF remote module to program the unit after the unit is placed inside an enclosed space. The remote 600 can stop a cycle, or program the unit to stop a cycle at a selected time. The remote 600 can allow a user to switch between the ozone generation cycle and the ozone degradation cycle. In some embodiments, the remote 600 allows a user to immediately terminate the ozone generation cycle before the end of the programmed run time. The remote 600 allows the user to immediately commence the ozone degradation cycle. The unit will start to remove ozone gas that has been generated. The ozone degradation cycle can be run for the amount of time that has been programmed by the user. The remote 600 can start the ozone degradation cycle or program. The remote 600 can stop the ozone generation cycle or program. The remote 600 can function to immediately stop the production of ozone. The remote 600 can function to immediately start degrading the ozone that has been created in the enclosed space. In some embodiments, an RF signal transmitted from the remote 600 to the unit function as an emergency shut off signal for the ozone generation cycle. The remote can include other functionalities. As one example, the remote 600 can include an alarm to signal the end of a cycle or program. Additionally, although embodiments of the remote module and the remote have been described as transmitting RF signals, communication paths using other technologies are feasible.

The remote 600 can include one or more features that prevent inadvertent commands. The remote 600 can require extension of an antenna to send a signal. The remote 600 can require the user to press a button to unlock the unit. The remote 600 can require the user to enter a code to unlock or turn on the unit. The remote 600 can require the user to hold a button to unlock the unit. The remote 600 can require the user to press a sequence of buttons to send a command via the remote 600.

The ozone sensor module can send and receive signals indicative of ozone concentration measured by an ozone sensor. The ozone sensor can detect low concentrations of ozone (e.g., less than 20 ppm, less than 10 ppm, less than 1 ppm, etc.). The ozone sensor can detect low concentrations of ozone after the ozone degradation cycle. The ozone sensor can detect high concentrations of ozone (e.g., more than 50 ppm, more than 100 ppm, more than 150 ppm, etc.). The ozone sensor can detect the peak concentration of ozone achieved during a sterilization event. The ozone sensor can detect that the ozone concentration is greater than a threshold during an ozone generation cycle. The ozone sensor can detect that the ozone concentration is greater than a maximum level detectable by the ozone sensor. The ozone sensor can detect that the ozone concentration is greater than a maximum recommended ozone concentration. The ozone sensor module can transmit signals indicative of these and other ozone measurements of the sensor.

The RFID reader module can receive signals related to the tracker. In some embodiments, the RFID reader module can send signals to and receive signals from the tracker. The RFID reader can receive a parameter related to the tracker (e.g., a tracker identification such as a name or serial number).

The sterilization unit 500 can include the corona array. The power module can include a transformer to convert the 110V power. The power to the corona array can be several orders of magnitude greater (e.g., 1 KV, 100 KV, 1000 KV, 10,000 KV etc.). The corona plate can include a steel mesh with silver inserts. The corona array can include 16 plates. The ozone can exit the sterilization unit 500 through operation of the ozone fans. The sterilization unit 500 can include three sets of fans.

The sterilization device 500 can be operated via a mobile app 700. The mobile app 700 can include one or more inputs, such as but not limited to buttons or icons, to control functions of the sterilization unit 500. The mobile app 700 can start a cycle, or program the unit to start a cycle at a selected time. The mobile app 700 can stop a cycle, or program. The mobile app 700 can start the ozone generation cycle or program. The mobile app 700 can start the ozone degradation cycle or program. The mobile app 700 can stop the ozone generation cycle or program. The mobile app 700 can stop the ozone degradation cycle or program. The mobile app 700 can set the programmed run time of the ozone generation cycle. The mobile app 700 can set the programmed run time of the ozone degradation cycle. The programmed run time can be an input to the sterilization device 500.

The mobile app 700 can include an indicator to signal the end of a cycle. The mobile app 700 can include an indicator to signal the end of the ozone generation cycle. The mobile app 700 can include an indicator to signal the end of the ozone degradation cycle. The mobile app 700 can include an indicator to signal that the unit is on. The mobile app 700 can include an indicator to signal that the mobile app has established a wireless communications path to a unit. The indicator can include a visual indicator (e.g., a colored light, a flashing light, etc.), an audial indicator (e.g., sound, alarm, beep, etc.), a tactile indicator (e.g., vibration), or other indicators known in the art.

The mobile app 700 can send signals to and receive signals from the sterilization unit 500. In some cases, the mobile app 700 transmits information to the sterilization unit 500 to program the unit before the unit is placed inside an enclosed space, such as information indicative of a sterilization program selected by the user using buttons or icons of the mobile app 700. The mobile app 700 can start a cycle, or program the unit to start a cycle at a selected time. The mobile app 700 can stop a cycle, or program the unit to stop a cycle at a selected time. The mobile app 700 can start the ozone generation cycle or program the unit to start the ozone generation cycle a selected time. The mobile app 700 can start the ozone degradation cycle or program the unit to start the ozone degradation cycle a selected time. The mobile app 700 can stop the ozone generation cycle or program the unit to stop the ozone generation cycle a selected time. The mobile app 700 can stop the ozone degradation cycle or program the unit to stop the ozone degradation cycle at a selected time a selected time. The remote can include other functionalities. As one example, the mobile app 700 can include an alarm to signal the end of a cycle or program.

The mobile app 700 can allow a user to switch between the ozone generation cycle and the ozone degradation cycle. In some embodiments, the mobile app 700 allows a user to immediately terminate the ozone generation cycle short of the programmed run time. The mobile app 700 allows the user to immediately turn the ozone degradation cycle on. The unit will start to remove ozone gas that has been generated. The ozone degradation cycle can be run for the amount of time that has been programmed by the user. The mobile app 700 can include one or more features that prevent inadvertent commands. The mobile app 700 can require the user to press a button to unlock the unit. The mobile app 700 can require the user to enter a code to unlock or turn on the unit. The mobile app 700 can require the user to hold a button to unlock the unit. The mobile app 700 can require the user to press a sequence of buttons to send a command via the mobile app 700.

In the embodiment depicted in FIG. 9, the ozone generator or corona array includes a plurality of pairs of ceramic plates 550. For example, in the top pair of plates depicted in FIG. 9, two ceramic plates 550 form a first pair of ceramic plates 555. The pair of ceramic plates 555 can be held in position via a holder 560. Each ceramic plate 550 of a pair of plates 555 is supplied with energy from the power module via post 525. A wall such as wall 530 can separate the ceramic plates 555 of an ozone generation cavity (such as the cavity enclosing the corona array shown in FIG. 9) from an ozone degeneration cavity (such as the cavity enclosing the scrub system shown in FIG. 9).

In some embodiments, at least one ceramic plate 550 of each pair of plates 555 can be at least partially coated or wrapped with a layer comprising a heavy metal. Particularly, at least one ceramic plate 550 of each pair of plates 555 is partially surrounded by a mesh 565. The mesh 565 can be a metallic mesh such as a stainless steel mesh. In the illustrated embodiment, each ceramic plate 550 of each pair of plates 555 is partially covered by a mesh 565. In the illustrated embodiment, only one side of each ceramic plate 550 is partially covered by a mesh 565 (e.g., side A). The opposite side of the ceramic plate 550 may not be covered by a mesh 565 (e.g., side B). In some embodiments, two or more sides of the ceramic plate 550 may be covered by a mesh 565 (e.g., side A and side B). In some embodiments, the ceramic plate 550 is encircled by a mesh 565 (e.g., at least side A and side B). In some embodiments, the ceramic plate 550 has at least two sides at least partially covered by a mesh 565. In some embodiments, the at least two sides are opposite sides of the ceramic plate 550. In some embodiments, each ceramic plate 550 of the corona array has at least two sides at least partially covered by a mesh 565. In some embodiments, the corona array has sixteen ceramic plates 550. In some embodiments, the corona array has thirty-two surfaces covered with a mesh 565.

The ceramic plates 555 are coupled to the holder 560 such that the mesh 565 of one ceramic plate 550 of a pair of plates 555 is adjacent to the mesh 565 of the other ceramic plate 550 of the pair of plates 555. The pair of plates 555 are coupled to the holder 560 such that the mesh 565 of one ceramic plate 550 of a pair of plates 555 faces toward the mesh 565 of the other ceramic plate 550 of the pair of plates 555.

Referring to the view of SIDE A, the mesh 565 can be coupled to a portion of the surface of the ceramic plate 550. In some embodiments, the mesh 565 is laminated to a portion of the surface of the ceramic plate 550. In some embodiments, the mesh 565 is bonded to a portion of the surface of the ceramic plate 550 with a bonding agent, such as silicon. In some embodiments, the mesh 565 forms a support structure for one or more heavy metal overlays 570.

The heavy metal overlay 570 can be coupled to a portion of the surface of the mesh 565. In some embodiments, the heavy metal overlay 570 is bonded to the mesh 565 with bonding agent 575. The bonding agent 575 can be silicon. The bonding agent 575 can bond the ends of the heavy metal overlay 570 to the mesh 565. In the illustrated embodiment, two strips of heavy metal overlay 570 are bonded to the mesh 565. Other configurations are contemplated (e.g., one mesh per plate, two meshes per plate, three meshes per plate, four meshes per plate; e.g., one heavy metal overlay per mesh, two heavy metal overlays per mesh, three heavy metal overlays per mesh, four heavy metal overlays per mesh; e.g., one mesh per pair of plates, two meshes per pair of plates, three meshes per pair of plates, four meshes per pair of plates etc.; e.g., one heavy metal overlay per plate, two heavy metal overlays per plate, three heavy metal overlays per plate, four heavy metal overlays per plate, etc.).

In some embodiments, the ceramic plate 550 is a rectangular shape with two long sides and two short sides. The heavy metal overlay 570 can form a strip. The heavy metal overlay 570 can be parallel to a long side of the ceramic plate. In some embodiments, the ceramic plate 550 can include two heavy metal overlays 570. Each heavy metal overlay 570 can be in the form a strip. Each heavy metal overlay 570 can be parallel to a long side of the ceramic plate. The heavy metal overlays 570 can be parallel. Other configurations are feasible. In some embodiments, the heavy metal overlay 570 can be disposed on only one side of the ceramic plate 550 (e.g., side A). In some embodiments, the heavy metal overlay 570 can be disposed on two sides of the ceramic plate 550 (e.g., side A and side B). The heavy metal overlay 570 can form any shape. The heavy metal overlay 570 can be round or polygonal. The cross-sectional area of the heavy metal overlay 570 can be selected based on the amount of heavy metal ions to be produced. The shape of the heavy metal overlay 570 can be selected based on the amount of heavy metal ions to be produced. The location of the heavy metal overlay 570 can be selected based on the amount of heavy metal ions to be produced. The number of heavy metal overlays 570 can be selected based on the amount of heavy metal ions to be produced.

Embodiments of the heavy metal overlay 570 can comprise any heavy metal, as described herein. The heavy metal overlay 570 can comprise silver. The heavy metal overlay 570 can be coated with a layer of pure silver. In some embodiments, the mesh 565 additionally or alternatively includes copper, nickel, cobalt, zinc, iron, gold, or any combination thereof. In some embodiments, the heavy metal overlay 570 additionally or alternatively includes copper, nickel, cobalt, zinc, iron, gold, or any combination thereof.

In such an arrangement, a ceramic plate 550 of each pair of plates 555 can form an anode and the other ceramic plate 550 of each pair of plates 555 forms a cathode. In operation, a high voltage is applied across the anode and cathode arrangement, creating an electric field between the each pair of plates 555. As air passes through the electric field between the each pair of plates 555, the oxygen molecules present in the air become excited and some dissociate, forming unstable oxygen atoms. The oxygen atoms then react with other oxygen molecules to form ozone. The heavy metal overlay 570 can function to produce heavy metal ions. In some embodiments, the application of a voltage across the pair of plates 555 also excites the heavy metal or metals of the heavy metal overlay 570. Such excitation may cause heavy metal ions to be produced and released into the enclosed space with the ozonized air. In the arrangement shown in FIG. 9, the application of a high voltage to the pair of plates 555 produces both ozone and heavy metal ions, such as silver ions. The sterilization unit 500 can be configured to produce a gas that includes both ozonized air and heavy metal ions. In some such embodiments, the sterilization unit 500 can be configured to produce a gas that includes ozonized air and silver ions.

One embodiment of the sterilization unit was used in a series of experiments to test the efficacy of the unit. The experimental methods and results are described briefly below.

Experiment 1

Figure 10A:
FIG. 10A provides a line graph of ozone level per hour, demonstrating the efficacy of the ozone generation and degradation unit of one embodiment.

In Experiment 1, an 1800 mg/hour ozone generator was placed in a 5.5 cubic feet cell culture. The ozone level within the chamber was monitored using a calibrated ozone analyzer. Ozone measurements were captured every 10 seconds. The experimental results, as represented by ozone level over time, are provided in the line graph of FIG. 10A. In test #1, represented by line 510, the ozone generator was run for 80 minutes and achieved a peak ozone concentration within the cell culture chamber of approximately 325 ppm. After the ozone generator was turned off, the ozone was left to break down naturally within the enclosed cell culture chamber. It took approximately 28 hours for the ozone to breakdown to 0.01 ppm ozone.

In tests #2 and #3, represented by lines 520 and 530, respectively, both the ozone generator and an ozone degrader were present in the cell culture chamber. The ozone degrader was formed of three activated carbon filters. With the ozone degrader present, the ozone generator was unable to achieve the peak ozone concentration seen in test #1. In tests #2 and #3, the ozone generator was run for 120 minutes and the concentration of ozone noticeably plateaued. The air within the cell culture chamber reached a peak ozone concentration of approximately 140-150 ppm ozone. After the ozone generator was turned off, the ozone began to break down at an accelerated rate with the activated carbon filters present. In both tests #2 and #3, the ozone levels reached a level of 0.01 ppm ozone within 15 minutes.

Figure 10B:
FIG. 10B provides a photograph of petri dishes demonstrating the results of an experiment testing the sterilization efficacy of one embodiment of an ozone generation and degradation unit.

While the peak ozone concentrations reached in tests #2 and #3 were noticeably lower than the peak ozone concentration of test #1, the ozone levels in tests #2 and #3 were at least sufficient to achieve sterilization. In each of tests #2 and #3, sterilization efficacy was measured with the assistance of LB agar plates loaded with E. coli bacteria. As part of the experiment, E. coli K-12 cells (strain DH5) were grown overnight at 37° C. and the stationary phase was reached. The following morning, 50 µL of the overnight culture (approximately $1.5 \times 10^8$ cells) were plated on each of three LB agar plates—two test plates and a control. A loaded agar plate was then included within each of the cell culture chambers for the duration of an ozone generation and degradation cycle (approximately 135 minutes). The agar plate was thus treated with ozone for 120 minutes and present for 15 minutes of ozone degradation within the cell culture chamber. The control plate was placed in a similar cell culture chamber for approximately 135 minutes with no ozone generator present. After each of these treatments, the plates were incubated at 37° C. overnight. The quantity of E. coli present was then analyzed and a photograph of each plate was taken. A photograph of the control dish 540 and the test dish 550 from test #2 is provided in FIG. 10B. As seen in the photograph, in the control dish 540, the E. coli experienced confluent growth. In the test dish 550, a 100% E. coli kill rate was observed; no E. coli was detected.

Experiment 2

In Experiment 2, the effect of ozone on bacteriophage T1 was studied. In the experiment, 2.5 µL of purified bacteriophage T1 was spotted in four quadrants of two LB agar plates—a test plate 610 and a control plate 620, shown in FIG. 11. The bacteriophage concentrations on each of the two plates were (clockwise from the spot in the upper right quadrant): $10^9$ pfu/mL, $10^8$ pfu/mL, $10^7$ pfu/mL, and $10^6$ pfu/mL.

The test plate 610 was placed in an incubator chamber containing both an ozone generator and an ozone degrader. The ozone generator included two ceramic plates surrounded substantially by a silver-coated metal mesh. The ozone generator was activated and the test plate 610 was treated with ozone for 4 hours. The ozone generator was then turned off, and the ozone degrader, formed of activated carbon filters, accelerated the conversion of ozone to oxygen. The peak ozone concentration level generated within the incubator chamber was less than 150 ppm ozone.

Figure 11:
FIG. 11 provides a photograph of petri dishes demonstrating the results of an additional experiment testing the sterilization efficacy of one embodiment of an ozone generation and degradation unit.

The control plate 620 was placed in a different incubator chamber and left untreated. After the ozone generation and degradation cycle completed in the incubator chamber containing the test plate 610, 1 mL of stationary DH5 E. coli bacteria and top agar were added to each plate and incubated at room temperature for 72 hours. The photograph in FIG. 11 was taken immediately following this 72-hour period. As shown in FIG. 11, the control plate contained active T1-phage in all four quadrants (see the clear areas, for example, the clear spot 622). Conversely, the ozone-treated test plate 610 showed negligible survival of the T1-phage.

For purposes of summarizing the disclosure, certain aspects, advantages and features have been described herein. It is to be understood that not necessarily all such advantages may be achieved in accordance with any particular embodiment. Thus, the invention may be embodied or carried out in a manner that achieves or optimizes one advantage or group of advantages as taught herein without necessarily achieving other advantages as may be taught or suggested herein. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. Thus, while the present disclosure has described certain practical embodiments, it is to be understood that the invention is not limited to the disclosed embodiments, but, on the contrary, is intended to cover various modifications and equivalent arrangements included within the scope of the appended claims, and equivalents thereof.

What is claimed is:

1. A method of sterilizing an enclosed space using ozone, the method comprising:
providing a portable sterilization unit, wherein the portable sterilization unit is configured to be positioned within an enclosed space, the portable sterilization unit comprising:
an ozone generator configured to ozonize air that enters the portable sterilization unit during an ozone generation cycle, and
an ozone degrader configured to remove ozone that enters the portable sterilization unit during an ozone degradation cycle;
wherein the portable sterilization unit is configured to execute stored programs for at least two different sterilization cycles based on a parameter selected from the group consisting of actual run time of the ozone generation cycle, actual run time of the ozone degradation cycle, programmed run time of the ozone generation cycle, programmed run time of the ozone degradation cycle, the volume of the enclosed space, the peak ozone concentration, and ozone generation intensity,
wherein a customer selects between the at least two different sterilization cycles and the portable sterilization unit is configured to run at least one ozone generation cycle and at least one ozone degradation cycle based on the customer selection,
wherein the portable sterilization unit records the parameter selected from the group consisting of actual run time of the ozone generation cycle, actual run time of the ozone degradation cycle, programmed run time of the ozone generation cycle, programmed run time of the ozone degradation cycle, the volume of the enclosed space, the peak ozone concentration, and ozone generation intensity,
wherein the portable sterilization unit generates a report based in part on the selected sterilization cycle, wherein the report comprises a display of differences between one or more parameters associated with the at least two different sterilization cycles; and
aggregating data over time related to two or more selected sterilization cycles by the customer.

2. The method of claim 1, wherein the report is generated periodically.

3. The method of claim 1, wherein the report aggregates data from sterilization cycles on different dates.

4. The method of claim 1, wherein the at least two different sterilization cycles have different run times of the ozone generation cycle.

5. The method of claim 1, wherein the at least two different sterilization cycles have different ozone concentrations.

6. The method of claim 1, wherein the report indicates the frequency of sterilization of the enclosed environment.

7. The method of claim 1, wherein the portable sterilization unit receives a data signal transmitted from the enclosed environment.

8. The method of claim 1, wherein the portable sterilization unit is controlled by a mobile app.

9. The method of claim 1, where a fleet of vehicles or a fleet of public transportation buses is sterilized.

10. A method of sterilizing an enclosed space using ozone, the method comprising:
providing a portable sterilization unit, wherein the portable sterilization unit is configured to be positioned within an enclosed space and sterilize the enclosed space, the portable sterilization unit comprising:
an ozone generator configured to ozonize air that enters the portable sterilization unit during an ozone generation cycle, and
an ozone degrader configured to remove ozone that enters the portable sterilization unit during an ozone degradation cycle;
wherein the portable sterilization unit is configured to execute stored programs for at least two different sterilization cycles based on run time of the ozone generation cycle or run time of the ozone degradation cycle, wherein a customer selects between the at least two different sterilization cycles and the portable sterilization unit is configured to run at least one ozone generation cycle and at least one ozone degradation cycle based on the customer selection,
wherein the portable sterilization unit records the run time of the at least one ozone generation cycle, the run time of the at least one ozone degradation cycle, or a total run time of the at least one ozone generation cycle and the at least one ozone degradation cycle;
wherein the portable sterilization unit generates a report based in part on the run time of the at least one ozone generation cycle, the run time of the at least one ozone degradation cycle, or the total run time of the at least one ozone generation cycle and the at least one ozone degradation cycle; and
aggregating data over time related to two or more selected sterilization cycles by the customer,
wherein the portable sterilization unit generates alerts related to maintenance based on aggregate data of two or more run times of the at least one ozone generation cycle of the portable sterilization unit, or aggregate data of two or more run times of the at least one ozone degradation cycle of the portable sterilization unit, or aggregate data of two or more total run times of the at least one ozone generation cycle and the at least one ozone degradation cycle of the portable sterilization unit.

11. The method of claim 10, wherein the report comprises identification of a location of the customer or identification of the enclosed space.

12. The method of claim 10, wherein the report is generated periodically.

13. The method of claim 10, wherein the report is aggregated from data of one or more trackers coupled to one or more portable sterilization units.

14. The method of claim 10, wherein the report comprises the date and start time of a sterilization cycle.

15. The method of claim 10, wherein the report comprises one or more parameters of a different sterilization cycle.

16. The method of claim 10, wherein sterilization is completed on demand.

17. The method of claim 10, wherein the report is generated automatically based on data recorded by the portable sterilization unit.

18. The method of claim 10, wherein an owner or an operating service of the portable sterilization unit generates the report automatically for the customer or a third party.

* * * * *